(12) United States Patent
Dettinger et al.

(10) Patent No.: US 8,620,688 B2
(45) Date of Patent: Dec. 31, 2013

(54) CHECKBOOK TO CONTROL ACCESS TO HEALTH RECORD BANK ACCOUNT

(75) Inventors: Richard D. Dettinger, Rochester, MN (US); Daniel P. Kolz, Rochester, MN (US); Richard J. Stevens, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 1720 days.

(21) Appl. No.: 11/241,704

(22) Filed: Sep. 30, 2005

(65) Prior Publication Data

US 2007/0075135 A1   Apr. 5, 2007

(51) Int. Cl.
*G06Q 50/00* (2012.01)
(52) U.S. Cl.
USPC ...................................... 705/3; 705/2; 705/51
(58) Field of Classification Search
USPC .................................... 705/2–4, 51
See application file for complete search history.

(56) References Cited

U.S. PATENT DOCUMENTS

| | | | |
|---|---|---|---|
| 5,867,821 A | 2/1999 | Ballantyne et al. | |
| 6,260,021 B1 | 7/2001 | Wong et al. | |
| 6,874,085 B1 | 3/2005 | Koo et al. | |
| 6,941,271 B1 | 9/2005 | Soong | |
| 6,988,075 B1 * | 1/2006 | Hacker | 705/3 |
| 2001/0053998 A1 | 12/2001 | Kohda et al. | |
| 2002/0004727 A1 | 1/2002 | Knaus et al. | |
| 2002/0010597 A1 | 1/2002 | Mayer et al. | |
| 2002/0010679 A1 | 1/2002 | Felsher | |
| 2002/0029157 A1 | 3/2002 | Marchoshky | |
| 2002/0169637 A1 | 11/2002 | Akers et al. | |
| 2003/0037054 A1 * | 2/2003 | Dutta et al. | 707/100 |
| 2003/0037059 A1 | 2/2003 | Yang | |
| 2003/0088439 A1 | 5/2003 | Grushka | |
| 2003/0115084 A1 | 6/2003 | Gage | |
| 2003/0177030 A1 | 9/2003 | Turner et al. | |
| 2003/0220817 A1 | 11/2003 | Larsen et al. | |
| 2004/0078236 A1 | 4/2004 | Stoodley et al. | |
| 2004/0093240 A1 | 5/2004 | Shah | |
| 2004/0199765 A1 | 10/2004 | Kohane et al. | |
| 2004/0236694 A1 | 11/2004 | Tattan et al. | |
| 2005/0159984 A1 | 7/2005 | Hirano et al. | |
| 2006/0184524 A1 | 8/2006 | Pollanz | |
| 2007/0078677 A1 | 4/2007 | Hofstetter | |
| 2007/0078684 A1 | 4/2007 | Dettinger et al. | |
| 2007/0078685 A1 | 4/2007 | Dettinger et al. | |
| 2007/0078686 A1 | 4/2007 | Dettinger et al. | |

(Continued)

OTHER PUBLICATIONS

Davis, M. W. (1993). Reaping the benefits of electronic medical record systems. Healthcare Financial Management, 47(6), 60-2, 64, 66. Retrieved from http://search.proquest.com/docview/196360811?accountid=14753.*

(Continued)

*Primary Examiner* — Mark Holcomb
(74) *Attorney, Agent, or Firm* — Patterson & Sheridan, LLP

(57) ABSTRACT

A method, apparatus, and article of manufacture for controlling access to electronic health records associated with an individual are provided. Individuals are provided with an electronic health records account (EHR account), wherein the EHR account is available to store electronic health records associated with the individual, in a network accessible storage repository. Additionally, an individual may be provided with plurality of disposable access devices, wherein the access devices may be presented to an entity. In turn, the entity may access the individual's EHR account, based on a predefined authorization specified for a particular access device.

22 Claims, 19 Drawing Sheets

(56) References Cited

U.S. PATENT DOCUMENTS

2007/0078687 A1 4/2007 Dettinger et al.
2007/0143148 A1 6/2007 Kol et al.
2007/0150315 A1 6/2007 Bennett et al.
2008/0215368 A1 9/2008 Shelton

OTHER PUBLICATIONS

Leier, Andre et al, "Cryptography with DNA binary strands", Apr. 14, 2000.

* cited by examiner

WITHDRAWL TRANSACTION

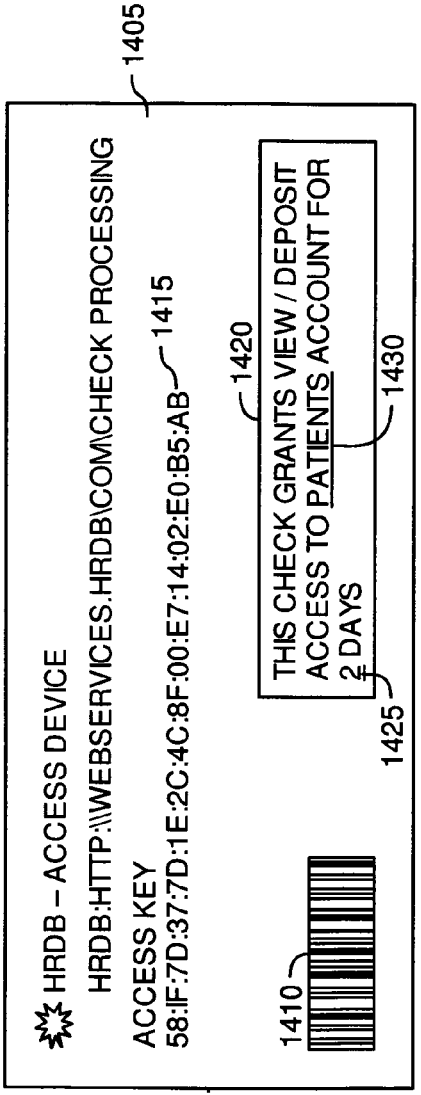
FIG 14A
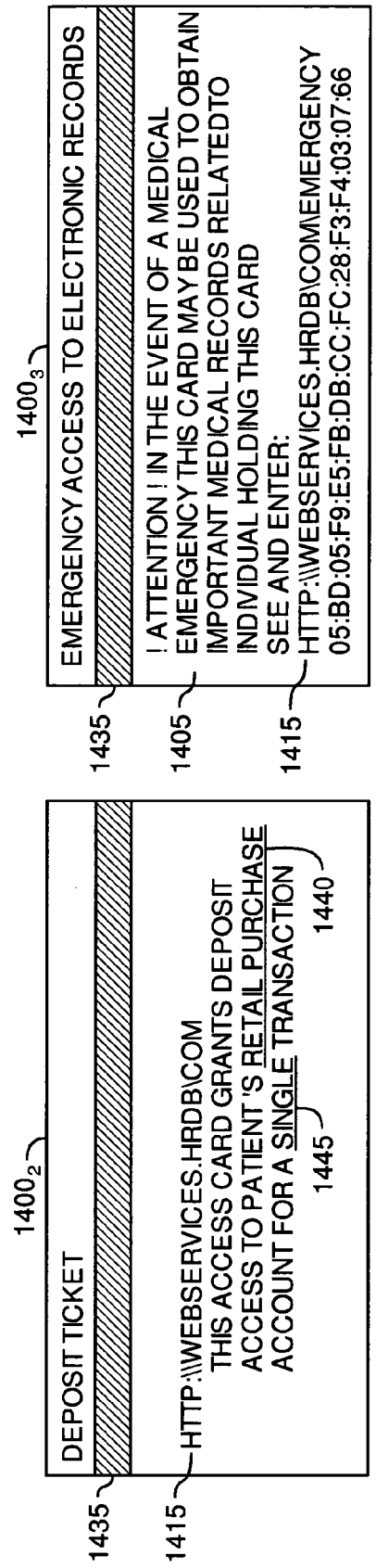
FIG 14C
FIG 14B

| Date | Record(s) | Requestor | Reason | Delegated From | Requestor Type | More Info |
|---|---|---|---|---|---|---|
| 01/13/03 | HDL/LDL Lab Test | Dr. Frank Smith | Appt | | Provider | |
| 03/24/04 | AST/ALT Lab Test «Drug X» Prescription | Medical Research Associates | Research Effects of «Drug X» on Liver Function | | Research | Findings |
| 04/15/04 | AST/ALT Lab test «Drug X» Prescription | ACME Pharmaceuticals | Research New Drug Clinical Trials | Medical Research Associates | Research | Clinical Trial |
| 05/11/04 | Blood Pressure (deposit) | Dr. Frank Smith | Appt | | Provider | Info on Treating Hypertension |
| ... | | | | ... | | ... |

FIG. 19

CHECKBOOK TO CONTROL ACCESS TO HEALTH RECORD BANK ACCOUNT

CROSS-REFERENCE TO RELATED APPLICATIONS

This application is related to the following commonly-owned, co-pending U.S. patent applications: "Managing Electronic Health Records Within a Wide Area Care Provider Domain," Ser. No. 11/241,707, "Electronic Health Record Transaction Monitoring," Ser. No. 11/241,706, "Multiple Accounts for Health Record Bank," Ser. No. 11/241,705, and "Business Models for Sustaining and Facilitating Participation in Health Record Data Banks", Ser. No. 11/241,703, each of which is filed herewith and incorporated herein by reference, in its entirety.

BACKGROUND OF THE INVENTION

1. Field of the Invention

The present invention generally relates to the electronic health records. More specifically, the present invention relates to methods for managing electronic health records stored by a healthcare records data bank that includes providing an individual with portable transferable access devices.

2. Description of the Related Art

Electronic data is pervasive; electronic data records have been created to capture details about almost any conceivable transaction or event. Medical records, for example, contain various data about patients, including medical history data, test data, medication data, etc. Electronic medical records (EMRs) have become a vital resource for doctors, researchers, laboratories, insurance providers, and claims-processors, etc.

One of the problems created by the proliferation of data is the management and accessibility of the data. Currently, electronic medical records are often stored by multiple unrelated entities, none of which are specialized in providing data storage or retrieval services. For example, a health care provider may maintain an internal set of electronic records for individual patients treated by the provider. Similarly, a pharmacist may maintain records for prescriptions dispensed to a patient at a particular location or pharmacy chain. Another health care provider, however, will not normally have on-demand access to the records of either. As illustrated by even this simple example, the electronic medical records related to a patient may be spread across many entities, and each entity is limited to accessing EMRs created by that particular entity.

Providing access to a complete collection of electronic medical records from this widely distributed data has proven to be very difficult. One proposed solution for creating a comprehensive EMR system involves creating a data federation. In such a federation, the electronic medical records related to a particular patient may be maintained at individual organizations (e.g., the healthcare provider, pharmacist, clinic, etc.), or at a number of repositories established to consolidate some EMR data. For example, the Cross Enterprise Document Sharing (XDS) profile (defined by the Integrating the Healthcare Enterprise (IHE) organization) is representative of a federated model. The XDS profile describes a clinical domain where institutions that join the domain share electronic medical records with one another. The clinical domain may include one to many data repositories storing electronic medical records.

Such models will typically rely on some form of federated query or retrieval operation when a request is made to view electronic health records for a given patient. That is, federated systems may respond to an EMR data request by (i) identifying each node that may include EMR data for the patient, and (ii) attempting to retrieve the relevant EMR data from each such provider node. The distributed nature of this model is a significant weakness, especially considering that many EMR systems used by healthcare providers are not designed to respond to what amounts to on-demand requests for patient data on a 24×7×365 basis. Thus, one substantial problem with this approach is that it requires a healthcare provider to become a data services organization. However, there is little economic incentive for many providers to invest in the equipment or personnel required to achieve an acceptable level of availability, security and reliability. Furthermore, many providers are reluctant to participate in a data federation due to fears of data security, and concern over regulatory compliance. Not surprisingly, attempts to build a federated model have largely failed due to both reliability issues (i.e., are all of the provider nodes available to respond to a given query?) and performance issues that arise, as EMR records must be individually retrieved from each provider node that stores such records.

Furthermore, the federated model may exclude non-traditional organizations from participating in the federation. For example, massage and physical therapists, whole-body scanning centers, vitamin and nutritional supplement providers, and even the individual to whom the records pertain, may not be able to contribute or access relevant electronic medical records to the federation. As approaches to healthcare treatment becomes more holistic, it would be advantageous if these types of non-traditional entities could contribute to a comprehensive heath care record associated with a particular individual, even though many such entities would most likely be prohibited from accessing most, if not all, of the EMR records.

Another problem with this approach is that the individual patient lacks any control over the EMR records created to store information about the patient. Furthermore, the patient has no awareness of how, or by whom, his/her data is being used.

Accordingly, there remains a need for a comprehensive EMR system. Such a system should be able to provide convenient access to a complete collection of electronic records related to the health care of an individual patient, regardless of the source of such records. Further, a comprehensive EMR system should provide a level or reliability, responsiveness and patient control/awareness that promotes the wide spread adoption of the system.

SUMMARY OF THE INVENTION

Embodiments of the invention provide patient-controlled access to an account of electronic medical records (EMR records). One embodiment of the invention provides a computer-implemented method of controlling access to a plurality of electronic medical records related to a plurality of individuals. The method generally includes configuring a network-accessible storage repository to store the plurality of electronic medical records, wherein the electronic records for a given individual are associated with an electronic health records account (EHR account), and providing the individual with at least one portable, transferable EHR account access device, wherein the access device authorizes an entity presented with the access device with access to the EHR account. The method generally further includes receiving, over a data-communications network, a request from the entity presented with the access device to access the EHR account, and based on a predefined authorization specified for the access device, performing at least one transaction for the EHR account.

Another embodiment of the invention provides a computer-readable medium containing a program, which when executed by a processor performs operations for managing access to a plurality of electronic medical records related to a plurality of individuals. The operations generally include configuring a network-accessible storage repository to store the plurality of electronic medical records, wherein the electronic records for a given individual are associated with an electronic health records account (EHR account), and providing the individual with at least one portable, transferable EHR account access device, wherein the access device is used to authorize an entity presented with the access device with access to the EHR account. The operations generally further include receiving, over a data-communications network, from the entity presented with the access device, a request to access the EHR account, and based on a predefined authorization specified for the access device, performing at least one transaction for the EHR account.

Still another embodiment of the invention provides a portable, transferable access device used to grant access to a network-accessible storage repository of electronic health records. The access device generally includes an electronic health records account (EHR Account) identifier, wherein the identifier specifies an individual associated with the EHR account, an access key for confirming that an entity requesting access to the network-accessible storage repository has been presented with access device by the individual, wherein the access key is included in a request, transmitted over a data-communications network, to access the EHR account, and an indication of the network location of the network-accessible storage repository.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments illustrated by the appended drawings. These drawings, however, illustrate only typical embodiments of the invention and are not limiting of its scope, for the invention may admit to other equally effective embodiments.

FIGS. 14A-14C illustrate an exemplary access check and two exemplary access tickets, according to one embodiment of the invention.

FIG. 19 illustrates one embodiment of a data processing environment in which fees are determined for data accesses made by a requesting entity.

DETAILED DESCRIPTION OF THE PREFERRED EMBODIMENTS

Figure 1:
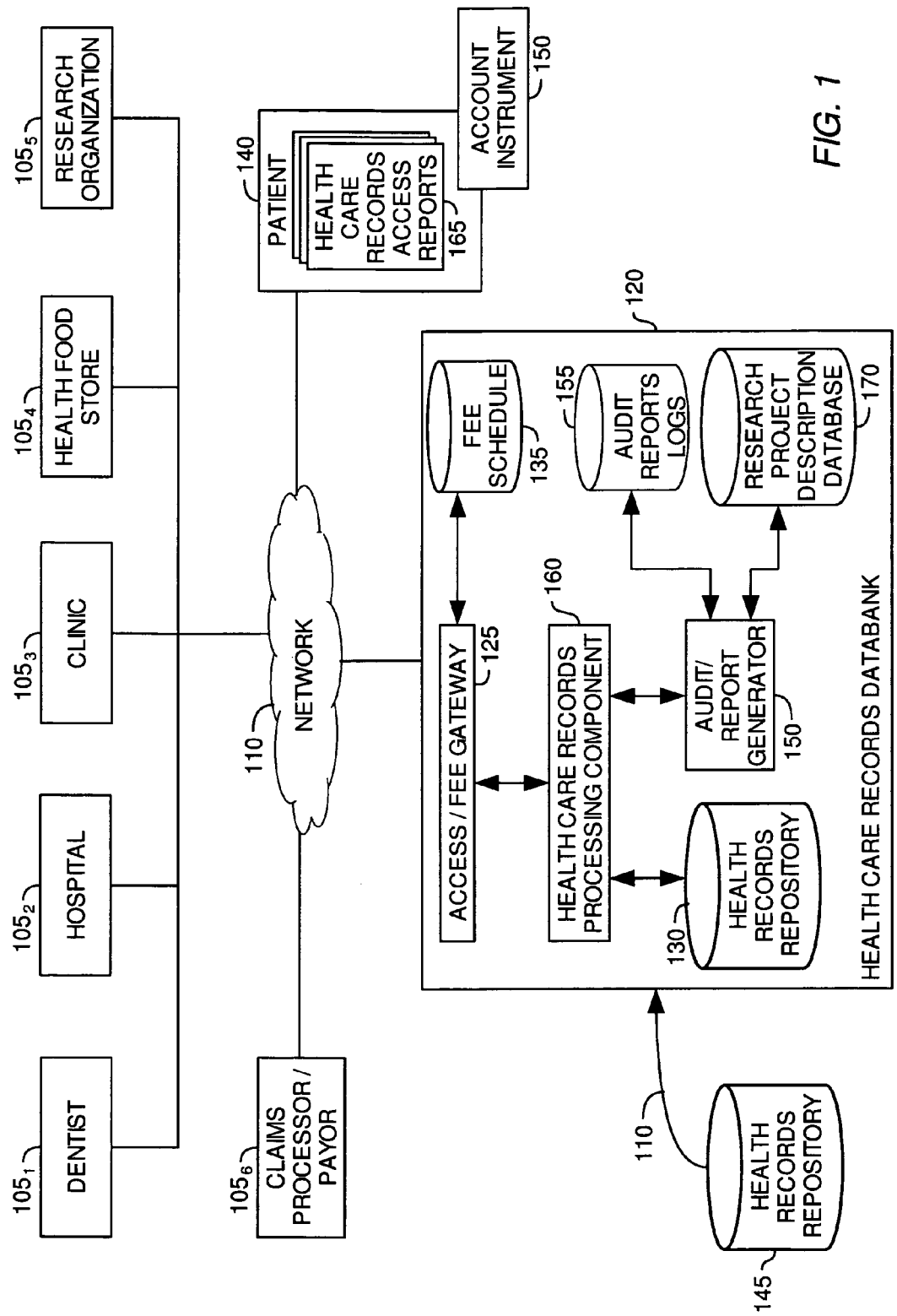
FIG. 1 is a functional block diagram illustrating a data communications environment, according to one embodiment of the invention.

Embodiments of the invention provide a method, system, and article of manufacture for creating and managing an electronic healthcare records data bank (HRDB). The HRDB may be configured to provide a patient-centric repository for the storage of a plurality of electronic medical records generated from a variety of sources. The patient's HRDB account may be accessed, for example, using an account instrument that identifies electronic medical account identifier (e.g., an account number), access information (e.g., an access key), and routing information (e.g., a network-accessible location) associated with the HRDB accounts. Once created, a variety of entities may initiate transactions with the HRDB account. Two common transactions include a deposit request used to add additional records to the individual's HRDB account, and a withdrawal transaction used to access and view records in the individual's HRDB account.

The following description references embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Further, reference made to "patients" is understood to mean any individual for whom data is being managed in an HRDB. The individual may or may not be currently undergoing treatment or testing for medical purposes. Further, the data corresponding to the individual may or may not have been derived from medical testing or treatment (e.g., the data may have been derived from a clinical trial in which the individual voluntarily participated). Consequently, reference to "medical records" includes data related to doctor's visits, lab tests, hospital stays, clinical trials, diagnoses (including self-diagnoses), prognoses, records related to the purchase of healthcare related goods and services such as nutritional supplements, weight-loss programs, alternative treatments such as chiropractic or acupuncture, etc.

Embodiments of the invention may be implemented, in part, using computer software applications executing on existing computer systems, e.g., desktop computers, server computers, laptop computers, tablet computers, and the like. The HRDB described herein, however, is not limited to any currently existing computing or data communications environment, and may be adapted to take advantage of new computing systems as they become available.

Further, embodiments of the invention may be implemented (including the methods described herein) as computer software applications and can be contained on a variety of computer-readable media. Illustrative computer-readable media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive); or (iii) information conveyed to a computer by a communications medium, such as through a computer or telephone network, including wireless communications. The latter embodiment specifically includes information across the Internet and other data communications networks. Such computer-readable media, when carrying computer-readable instructions that direct the functions of the present invention, represent embodiments of the present invention.

In general, program routines created to implement an embodiment of the invention may be part of an operating system or a specific application, component, program, module, object, or sequence of executable instructions performed by a particular computing system. In addition, various computer software applications described hereinafter may be identified based upon the application for which they are implemented in a specific embodiment of the invention. However, it should be appreciated that any particular program nomenclature that follows is used merely for convenience, and thus the invention is not limited to use solely in any specific application identified and/or implied by such nomenclature.

Embodiments of the invention provide a patient-centric method for managing electronic medical records. In one embodiment, a health record data bank (HRDB) is configured to store electronic medical records associated with a plurality of individual patients. The HRDB securely stores a comprehensive collection of health records associated with a particular individual, and further allows an individual patient to control who may have access to those records.

In one embodiment, the organization operating the HRDB may also be the medical care provider that generates the EMR records. In another embodiment, the organization operating the HRDB may be independent from the entities providing medical care. In the latter case, it is contemplated that multiple HRDBs may exist and compete so that individual patients are free to choose a HRDB satisfying their own personal quality-of-service versus cost criteria. Furthermore, because the HRDB may provide services for a fee, multiple HRDBs may compete with one another for individual accounts.

Unlike a federated system that requires the maintenance of a registry to identify the location of each electronic record associated with a given patient, healthcare providers and research institutions may retrieve the electronic medical records associated with a given patient from a single HRDB. Similarly, the HRDB provides a centralized entity for healthcare providers (or other relevant information producers) to submit EMR records to the HRDB for deposit. Patients are provided choice and control over where and how their electronic health records are maintained, alleviating at least some of the privacy and control issues that are a current obstacles to EMR system deployment.

In one embodiment, a healthcare records bank (HRDB) provides a data repository for the storage of medical records. The actual HRDB records may include any information related to the patient that may be represented in a digital form and stored in a storage device. Accordingly, text documents, images (e.g., x-rays or other imaging data) lab-test results, doctor's notes, insurance information, patient observations, and the like, may all be included in a patients HRDB account. Further, the individual may authorize various transactions, including the deposit or withdrawal of EMR records. For example, requests made by health care providers or medical research institutions to view an individual's records may be serviced by the HRDB subject to any access constraints specified by the individual. For example, in one embodiment, an individual may configure multiple accounts with the HRDB, each account being associated with a specific set of electronic medical records. By granting access to a specific account, the individual may allow a provider to access only the records associated with that account.

A HRDB will typically support a variety of transactions related to the EMR records for a particular patient. For example, healthcare providers may be allowed to deposit electronic records into a patient's account. A deposit transaction results in the deposited electronic record being stored in the data repository provided (or controlled) by the HRDB. These deposits may be in an encrypted format. In one embodiment, an individual authorizes a healthcare provider to transmit a deposit transaction request to the HRDB. The deposit request includes the patient's authorization to deposit records into the patient's HRDB account, along with the electronic record for deposit. Additionally, the HRDB enables additional types of EMR record transactions, including deposits representing self-observations or other information provided by the individual patient (e.g., the individual may deposit records into the HRDB indicating the use of a particular over-the counter-medication on a regular basis, or deposits of EMR records reflecting purchases made at a vitamin and nutritional supplements provider).

As stated, one contemplated transaction is a deposit transaction. In one embodiment, the HRDB would accept and deposit records into an individual's HRDB account only if authorized by the individual patient. Thus, the HRDB provides a patient with control over what organizations may deposit EMR records into an HRDB account.

Another contemplated transaction includes a withdrawal transaction. In one embodiment, an HRDB allows a healthcare provider to request to view the EMR records associated with a given patient. Alternatively, a patient may define multiple accounts, each containing a subset of the overall EMR records in the account and allow a healthcare provider to view the records included in a particular account.

Withdrawal request may be generated by a healthcare providing organization that needs access to prior medical history in treating a patient. Detailed examples of both deposit and withdrawal transactions briefly described above are provided, below. Additionally, an individual may be provided with a network-based interface to view any of the records currently stored in his/her HRDB account. For example, the HRDB may provide a network-accessible interface, e.g., a webpage accessed using a web browser. To access his/her HRDB account, an individual may be required to provide an account identifier and password, or use some from of access mechanism, e.g., a credit-card type object with a magnetic strip encoding HRDB account information.

FIG. 1 is a functional block diagram illustrating an exemplary computing and data communications environment 100, according to one embodiment of the invention. FIG. 1 provides a high-level view of multiple entities $105_{1-6}$ in communication with healthcare records databank (HRDB) 120 over a data communications network 110. In one embodiment, each of the entities $105_{1-6}$ may include any healthcare related entity with a computing system connected to network 110. While providing healthcare related goods or services, an individual patient 140 may authorize an entity 105 to deposit EMR records with the HRDB 120. Illustratively, the entities 105 represented in FIG. 1 include a hospital $105_2$, a clinic $105_3$, a research organization $105_5$, a health food store $105_4$, a dentist $105_1$, and a claims processor $105_6$. More generally, each entity $105_{1-6}$ represents a real-word location where an individual may seek, obtain or receive healthcare related goods or services for which electronic medical records may be generated and deposited with the HRDB 120. Additionally, the patient 140 may authorize entities 105 to submit a withdrawal request to view EMR records stored in the HRDB 120.

Patient 140 represents the individual owner/subscriber that controls access to the EMR records stored in a particular HRDB account. In one embodiment, a patient 140 may enter into a contractual relationship with a selected HRDB 120. Additionally, the HRDB 120 may provide patient 140 with an access mechanism to view the content and status of the individual's HRDB account, along with a report of deposit/withdrawal requests. For example, in one embodiment, the HRDB 120 may periodically provide a healthcare records access reports 165 (e.g., monthly) detailing account activity. Alternatively, an individual may view access reports on-line (e.g., using a web-browser communicating with the HRDB over network 110).

In one embodiment, deposit and withdrawal transactions are authorized by a patient using an account instrument 150. The patient 140 uses the account instrument 150 to authorize HRDB transactions and identify the HRDB 120 selected by the patient. For example, the account instrument 150 may be an "access card" that includes a magnetic strip that encodes information identifying the patient's account and the particular HRDB provider, (e.g. a public/private key pair provided by an x.509 digital certificate and the network-accessible location of the HRDB). In one embodiment, the patient 140 uses the account instrument 150 to authorize an entity 105 to engage in transactions to view and/or deposit EMR records into the patient's HRDB account. In another embodiment, the account instrument 150 may comprise a token device used to store a radio frequency identification (RFID) tag, flash-memory device, or smartcard. In such a case, an entity 105 may retrieve the access key from the account instrument 150 using an appropriate receiver or reader (e.g., an RFID tag receiver, or smartcard reader).

In another embodiment, the account instrument 150 may provide a patient 140 with a set of access keys, each of which grant the holder of the key some predefined level of access to an individuals HRDB account. Each key may be configured to grant access to a patient's HRDB account for a specific period of time. This allows the patient 140 to grant access to EMR records in HRDB 120 to an entity 105 with no preexisting relationship with a particular HRDB 120. For example, each key may include single-use, or disposable, "access card" devices with an encoded magnetic strip. Once the patient 140 provides an entity 105 with the access card, the entity 105 may deposit and withdraw electronic records to/from the patient's HRDB account, according to the constraints specified for the particular card. Alternatively, an access key may be a character sequence entered on a web-interface by the provider 105 to obtain access to a patient's HRDB account.

In addition, the HRDB 120 may require the individual to provide a personal identification number (PIN) or other form of an account access code before the entity 105 will be allowed to access the individual's HRDB account using one an access check. For example, the entity 105 may use a keypad type device that allows the individual to key in a PIN number transmitted to the HRDB 120 along with a request from the entity 105 to access the individual's HRDB account.

In one embodiment, the HRDB 120 is configured with the necessary computing resources to process transaction requests from any of the relevant entities 105. Illustratively, the HRDB 120 is shown including an access/fee gateway 125, healthcare records processing system 160, a health records repository 130, and a health record audit history repository 155, audit/report generator 160, and a research project description database 170. The access/fee gateway 125 may be configured to process connection requests from any of the entities 105. In one embodiment, the access/fee gateway 125 is configured to determine a fee for a given transaction. The fee may be determined or calculated on the basis of one of more fee schedules 134 stored in fee database 135. In one embodiment, the access/fee gateway 125 may identify the account subscriber named in a request, verify the authenticity of the request, and log the request with the health record audit history repository 155. The logs contained in the repository 155 may be used to process and record data related to fee-based services provided by the HRDB 120. Additionally, audit/report generator 160 may be configured to generate a record of activity for particular HRDB account, or the activity of a research organization $105_5$. For example, the HRDB 120 transmit (e.g., periodically or upon request) an account statement 165 to each individual with an HRDB account via (e.g., via e-mail or U.S. postal service), as will be described in more detail below.

Additionally, in one embodiment, the HRDB 120 may be configured to validate a request to deposit an EMR record into an HRDB account using a validation service provided by a claims processor $105_6$. For example, when a clinic $105_3$ treats an individual patient 140, a claim may be submitted with the patient's insurance company. Insurance information may also be encoded on the HRDB account instrument 150. Often, a clinic $105_3$ will submit insurance and claims information to a claims processor $105_6$. The HRDB may verify that a given deposit corresponds to an insurance claim actually filed on behalf of the patient, 140.

The healthcare records processing component 160 may provide a computing environment that includes the appropriate computer systems (both hardware and software) configured to control and manage the data repositories and transaction services supported by the HRDB 120. In one embodiment, data repositories 130, 135, 155, and 170 may be relational database systems configured to store data according to a schema of related tables and columns, queried using the known SQL query language. However, other storage formats may be used.

Healthcare records processing component 160 may include a variety of relational database management systems to process SQL queries. The healthcare records repository 130 may be used to store the actual EMR records generated by the various entities 105, for a plurality of patients. As described above, the electronic medical records may include any data related to the patient 140 that may be represented in a digital form and stored in data repositories 130. Illustrative examples include text documents, spread-sheets, database records, XML data, imaging data (e.g., x-rays CT scans, NMR imaging, or other imaging data) lab-test results, doctor's notes, insurance information, patient observations, purchase records, etc. However, the HRDB 120 may receive deposits of EMR records regardless of format, and is capable of storing any form of data submitted by entity 105 or patient 140. Furthermore, the invention not limited to any particular computing environment 160, and data repositories 130, 135, 155, and 170 and may be adapted to take advantage of new computing systems and electronic data storage mechanisms as they become available.

In one embodiment, the HRDB 120 may store EMR records remotely in an off-site health records repository 145. Thus, the actual EMR records for an individual patient 140 need not be physically stored at the location of HRDB 120, so long as the healthcare records processing component 160 is configured to retrieve the records for a particular patient 140 from the repository 145 in response to a withdrawal transaction request, and to deposit electronic medical records in response to a deposit request.

Figure 2:
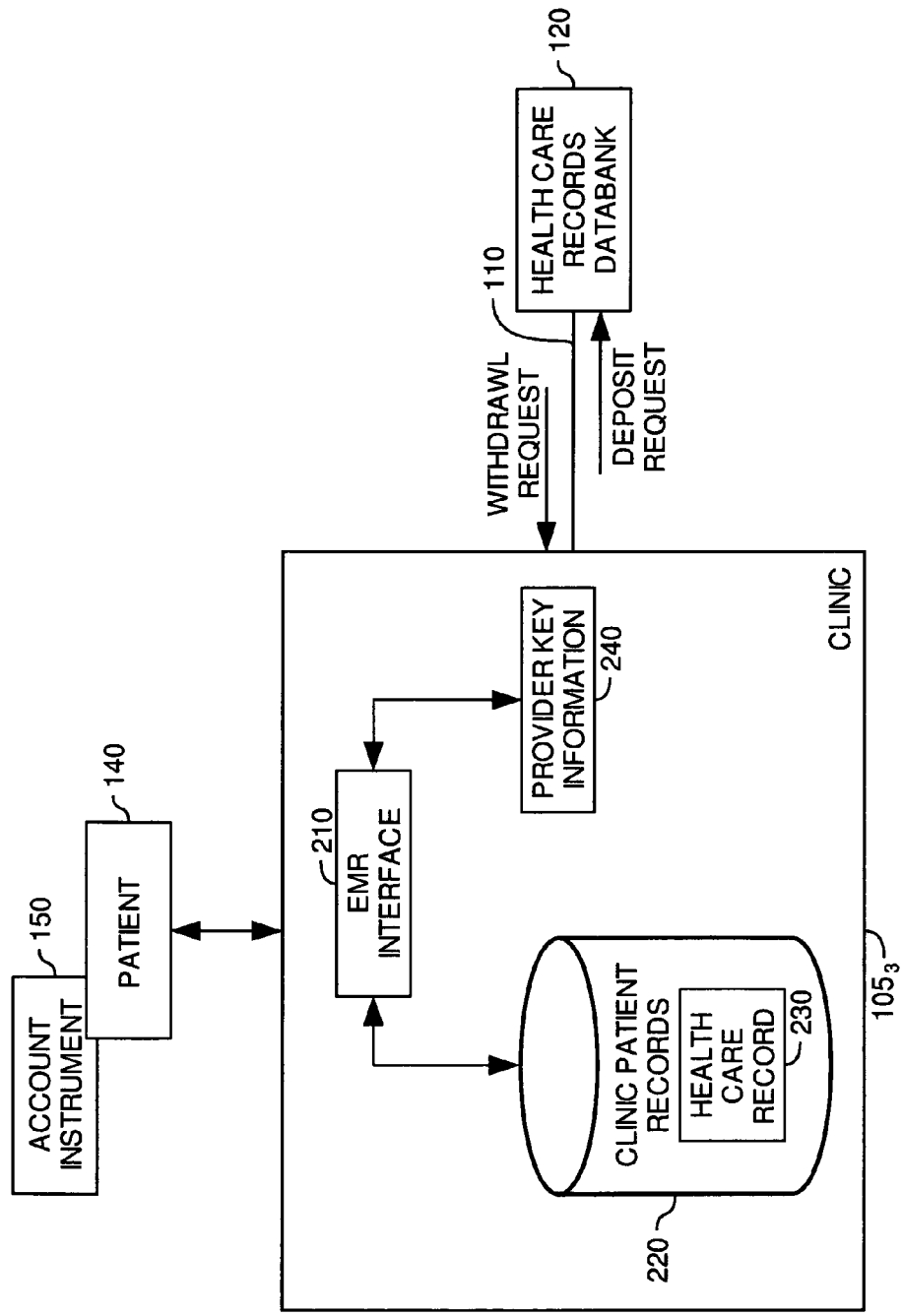
FIGS. 2-4 are functional block diagrams further illustrating elements of the data communications environment first illustrated in FIG. 1, according to one embodiment of the invention.
Figure 3:
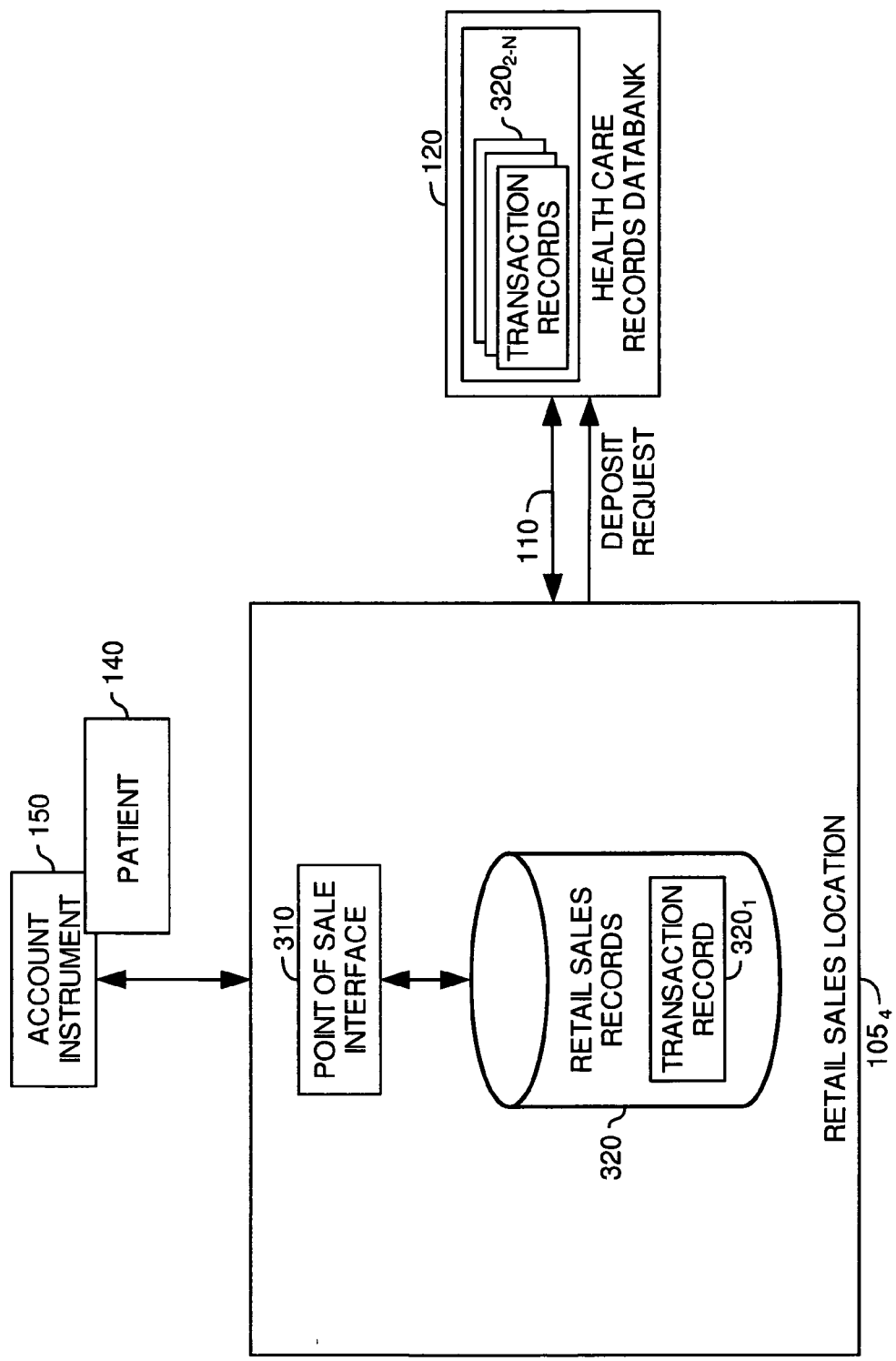
Figure 4:
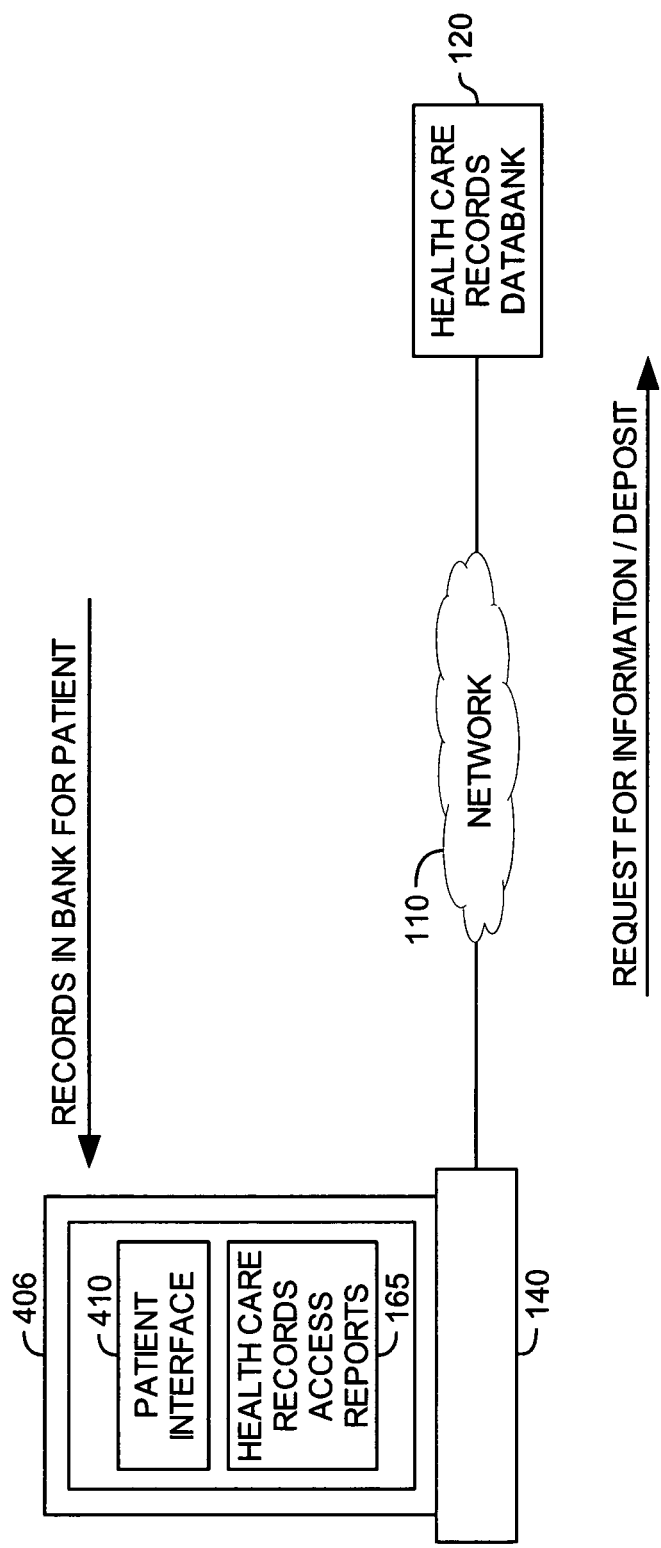

FIGS. 2-4 illustrate examples of entities 105 where a patient 140 may obtain healthcare related goods or services for which EMR records may be generated and deposited with the HRDB 120, or where a patient 140 may authorize an entity 105 to withdraw and view records from the patient's HRDB account.

FIG. 2 is a functional block diagram illustrating a healthcare providing entity $105_3$, according to one embodiment of the invention. In one embodiment, the patient 140 may provide the account instrument 150 to a physician, nurse, or other representative at a medical clinic $105_3$. Typically, a clinic $105_3$ will use an EMR interface 210 to obtain the account information from account instrument 150, and to generate transaction requests transmitted to HRDB over network 110. For example, the interface 210 may be an electronic card reader or token device reader configured to "read" the information encoded on an account instrument 150 such as an access card, RFID token device, or smartcard. Alternatively, the EMR interface 210 may include a computer system connected to network 110, wherein a clinic representative enters the account and routing information provided by account instrument 150 to access the individual's HRDB account. Additionally, if an access code is required (e.g., a PIN number), the EMR interface 210 may be configured to allow a user to key in his/her access code.

In one embodiment, provider key information 240 may include cryptographic keys used to authenticate the identity of the clinic $105_3$ to HRDB 120. Any known or later developed cryptographic protocol may be used. In treating a patient 140, the clinic may submit both withdrawal requests to view EMR records, as well as deposit requests to add new records to the patient's HRDB account. Illustratively, the clinic $105_3$ includes a clinic data repository 220 configured to store EMR records 230 related to patients treated at a given clinic $105_3$. These records represent the clinic's internal electronic records. In addition, EMR records generated by the clinic may be deposited with the HRDB 220. Similarly, a dentist $105_1$, hospital $105_2$, or emergency room, may all engage in transactions using account instrument 150, EMR interface 210, and provider key information 220 to generate deposit and withdrawal requests processed by the with the HRDB 120.

FIG. 3 is a functional block diagram further illustrating a healthcare providing entity $105_3$, according to one embodiment of the invention. Illustratively, entity $105_4$ represents a retail sales location from which a patient may purchase healthcare related goods or services. For example, entity $105_4$ may comprise a medical supply store selling oxygen canisters, or a nutritional supplements provider selling vitamins or herbal remedies. In one embodiment, the purchaser of such goods (e.g., patient 140) may provide account instrument 150 to point of sale interface 310. (e.g., a magnetic card reader). For example, the interface 310 may be an electronic card reader configured to "read" the information encoded on an access card (i.e., account instrument 150). The point of sale interface 310 may be configured to generate an electronic transaction record 320 (e.g., an electronic copy of a purchase receipt) deposited using a deposit request in the patient's HRDB account 120.

FIG. 4 is a functional block diagram illustrating a patient 140 using a computer system 400 to access his/her account with an HRDB 120, according to one embodiment of the invention. Illustratively, computer system 400 may be a personal computer system connected to a network 110, such as the internet. The patient interface 410 allows an individual to view data records stored in the HRDB 120. In one embodiment, an individual (e.g. patient 140) authenticates his/her identity to the HRDB 120 using account instrument 150. As described above, the instrument 150 may include cryptographic keys encoded on instrument 150 accessed by a card-reading device. Alternatively, a patient may provide a username/password to identify an HRDB account and verify his/her identity with the HRDB 120. Once authenticated, a user may view any records stored in the HRDB 120 (associated with that individual's particular account).

In a specific embodiment, the patient interface 410 may be provided using a web-browser (e.g., the Firefox web browser available from the Mozilla® foundation or the Internet Explorer® web browser available from Microsoft® corp.) Using the web-browser allows EMR records to be exchanged between the HRDB 120 and patient 140 using standardized protocols (e.g., HTML, XML, XHTML, DHTML etc). However, embodiments of the invention may be adapted to other methods of network data exchange as they become available.

Additionally, in one embodiment, the user interface 410 may be configured to allow an individual to create and deposit new records in to his/her HRDB account. Such records could indicate, for example, what over-the-counter medications a person has ingested, or allow the patient 140 to create EMR records detailing how well an individual is following or responding to an exercise or treatment regimen prescribed by an healthcare providing entity 105.

Figure 5:
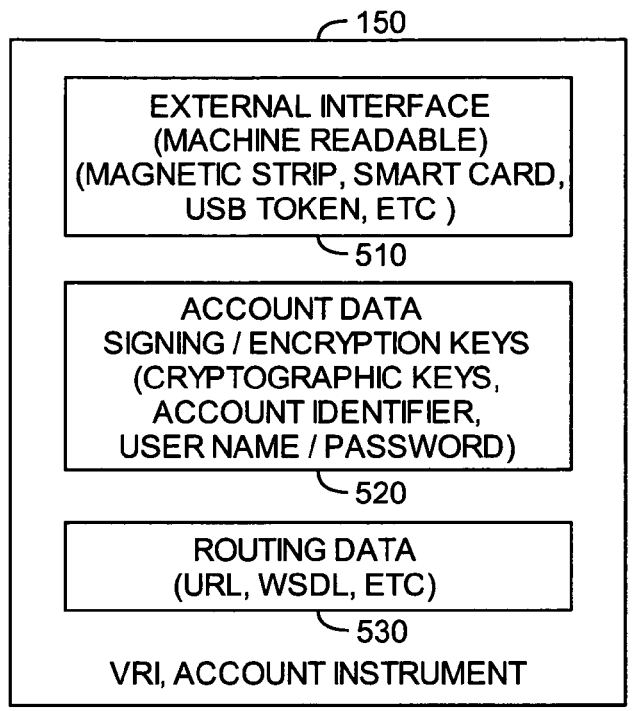
FIG. 5 illustrates account instrument used to authorize account transactions with a health care records data bank, according to one embodiment of the invention.

FIG. 5 illustrates an account instrument 150 used to authorize account transactions with a HRDB 120, according to one embodiment of the invention. As illustrated, the account instrument 150 includes an external interface 510, account data 520, and routing data 530.

In one embodiment, account instrument 150 may provide a patient 140 with a portable access device that encodes account data 520 and routing data 530 in a machine-readable form. For example, the machine readable interface 510 may be a magnetic strip, smart-card, USB token device, barcode, or 3D barcode, scanned by a device at entity 105 (e.g., EMR interface 210, point-of-sale interface 310, or user interface 410). Alternatively, the account instrument 150 may be information manually input to a computer such as a set of written instructions specifying routing data 530 and an authentication data 520 (e.g., a URL, account identifier and access passwords or codes) that must be supplied to authorize request submitted to the HRDB 120 regarding a patient's account.

Figure 7:
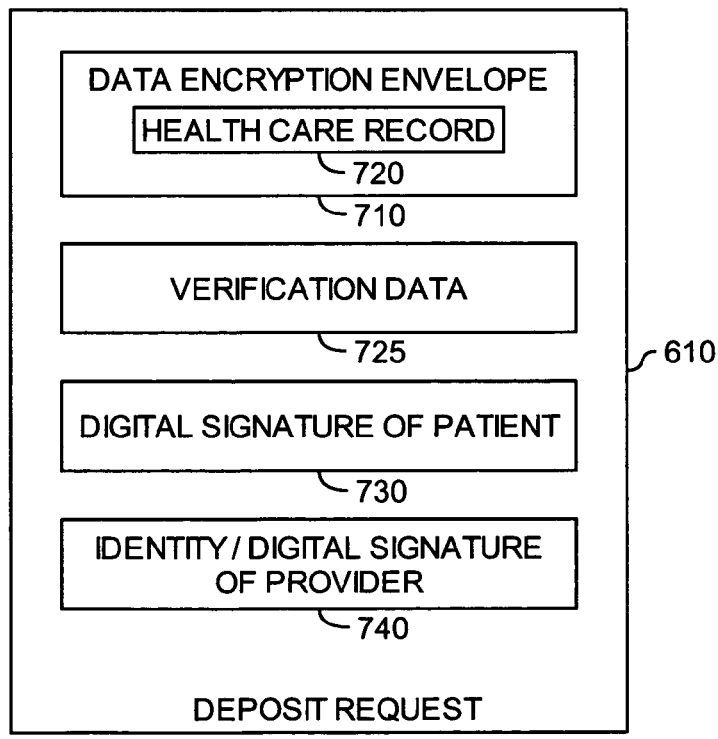
FIG. 7 illustrates an embodiment of a deposit record data structure.
Figure 6:
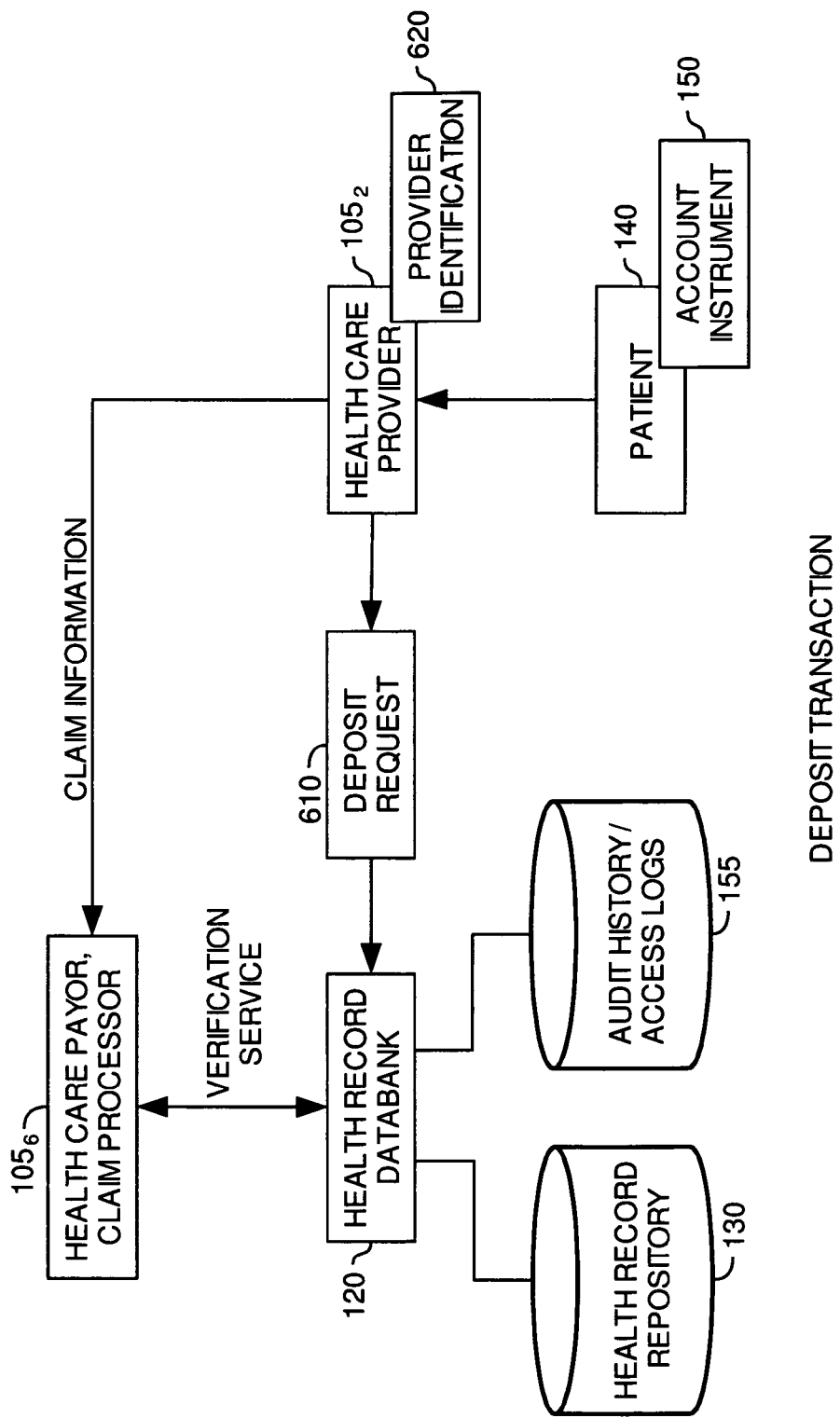
FIG. 6 is a functional block diagram illustrating a health care record deposit transaction, according to one embodiment of the invention.
Figure 8:
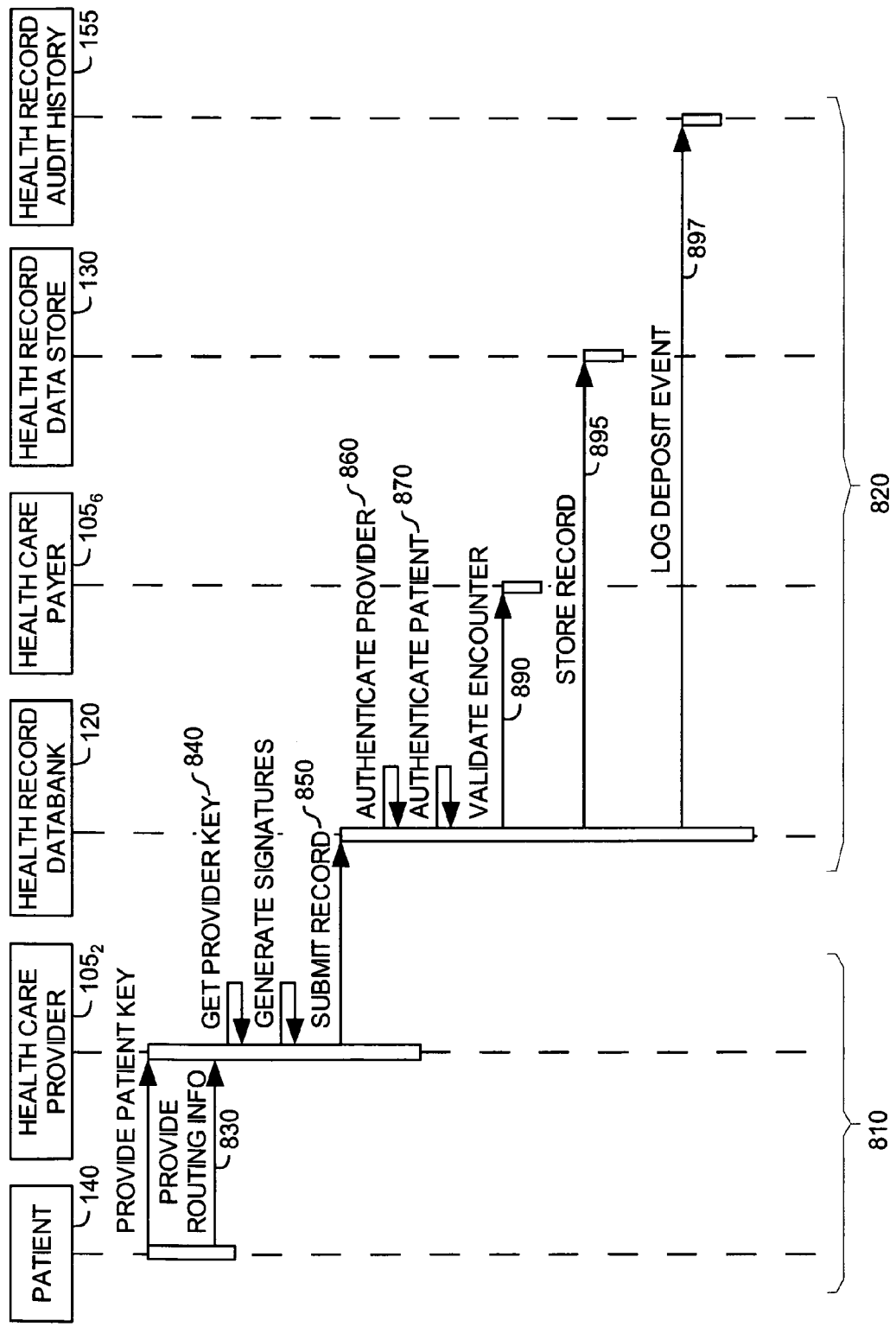
FIG. 8 illustrates a method for performing a deposit transaction with a health care records data bank, according to one embodiment of the invention.
Figure 9:
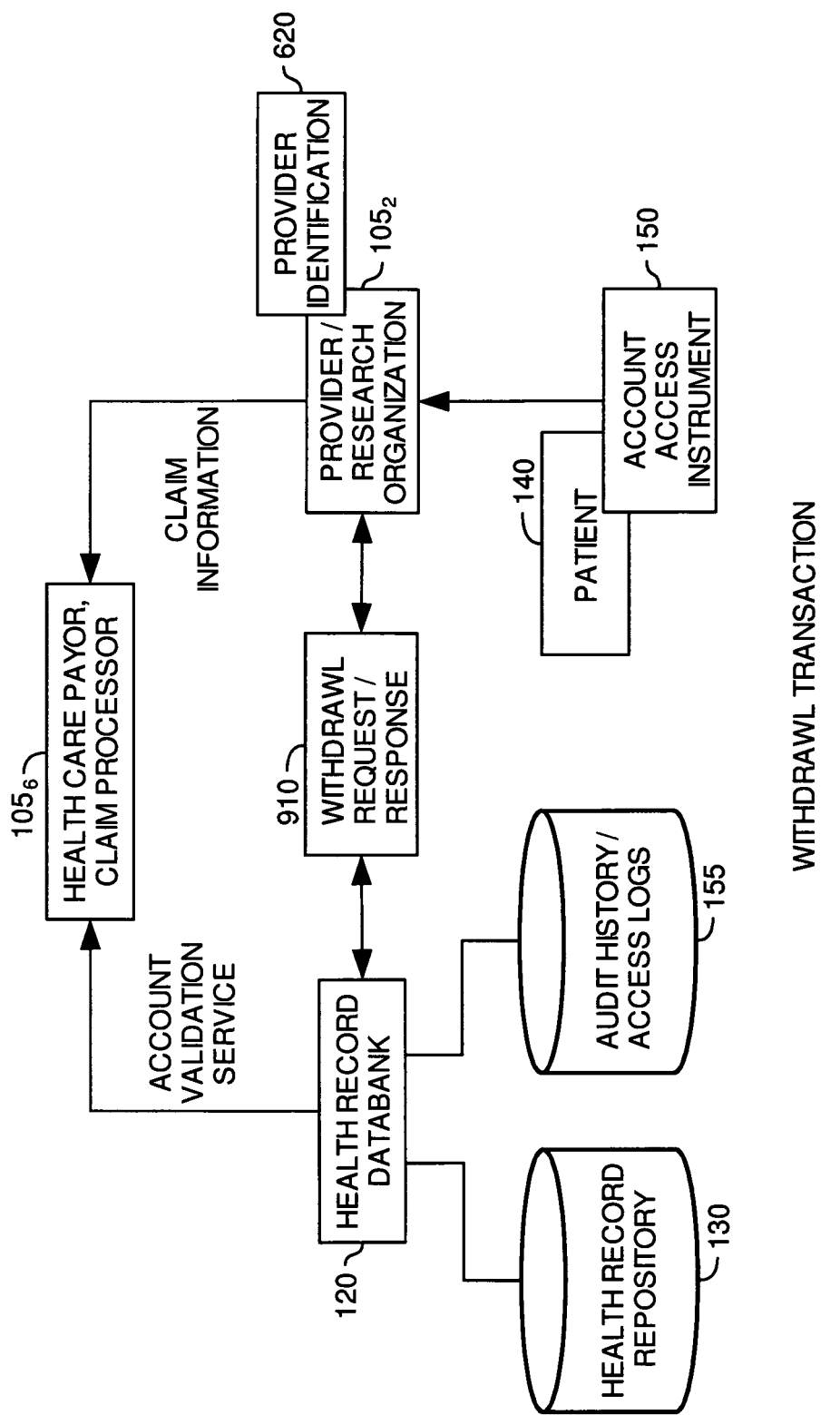
FIG. 9 is a block diagram illustrating interacting components used for a withdrawal transaction, according to one embodiment of the invention.

Routing data 530 may be used to identify a network-accessible location for the HRDB 120. In various embodiments, the routing data 530 may be specified using a universal resource locator (URL) web-service address, FTP location, or other information specifying a method for an entity 105 to establish a data communications connection over a network 110. Illustratively, Account data 510 includes a digital certificate or cryptographic key pairs used to authenticate a deposit or withdrawal transaction request. For example, the key data 520 may include an encryption key (used to encrypt a request/data transmitted to the HRDB 120) and a digital certificate and signature key (used to validate that a transaction request is authorized by the patient 140). Accordingly, in one embodiment, the key data 120 may include digital certificates generated and configured according to the x.509 standard for digital certificates developed by the International Telecommunications Union (ITU). However, other cryptographic protocols or standards may be used. Alternatively, a patient may authorize a transaction request using an account identifier or password or personal identification number. For example, a patient may authorize a transaction request using an account card "swiped" by a magnetic-card reader and enter in a personal identification number Using the components illustrate in FIGS. 1-5, FIGS. 6-11 illustrate two common transaction services that may be provided by an HRDB. FIGS. 6-8 illustrate a deposit transaction used to add new records to the HRDB 120. FIGS. 9-11 illustrate a withdrawal transaction used to obtain and view EMR records stored by the HRDB 120.

Referring first to FIG. 6, a functional block diagram is shown illustrating components of a distributed environment 600 used to initiate a deposit transaction with an account HRDB 120, according to one embodiment of the invention. Illustratively, the distributed environment 600 includes health care provider $105_2$ (also shown in FIG. 2), interacting with patient 140 and account instrument 150. In one embodiment, when patient 140 receives healthcare related goods or services from provider $105_2$, the patient provides the account access instrument 150 to provider $105_2$ to authorize a deposit request 610. In one embodiment, the deposit request 610 may be generated from use account data 520 and routing data 530. Additionally, provider identifier 620 may be used to identify the physician or provider 105 making the deposit request. Deposit request 610 includes the relevant EMR records to be deposited in the HRDB. Once generated, signed, and transmitted, the HRDB 120 may be configured to process the deposit request 610 by verifying the identity of the requesting entity (using provider identifier 620 and account instrument 150) and deposit the EMR records into the appropriate account. Optionally, in one embodiment, the HRDB 120 may be configured to use a verification service offered by a claims processing service, $105_6$. In such an embodiment, the HRDB 120 may verify that the deposit corresponds to an insurance or other healthcare claim filed with the claims processor $105_6$.

Additionally, audit/history logs contained in the repository 155 may record the identity of the entity 105 depositing new EMR records into a patient's HRDB account. Thereafter, when such EMR records are the subject of a withdrawal transaction, or when a heath record access report 165 is provided to the patient 140, this information may be provided with the corresponding EMR records. Thus, in addition to a comprehensive collection of electronic medical records, a patient's account may also include meta-information identifying what entity 105 deposited a particular record, what entity 105 has viewed records, and other logging data describing transactions that have occurred. In addition to providing a patient 140 with a reconciliation of account activity, information from the audit/history logs contained in the repository 155 may be useful for evaluating the validity or accuracy of specific record within the patient's account (e.g., an assertion that the patient was exhibiting chest pains typical of a heart attack may be more persuasive coming from a cardiologist than from the patient him/herself or from a general practitioner).

FIG. 7 illustrates one embodiment of a deposit request data structure 610. Illustratively, the request data structure 610 includes a data portion 710, and authentication portions 730 and 740. In one embodiment, the data portion 710 represents the EMR record associated with the deposit request. In other words, the electronic record being deposited. As illustrated, the healthcare record 720 is shown enclosed within an encryption envelope. As described above, public key cryptography (PKI) techniques may be used by the HRDB 120 to help provide data security, authenticity, and integrity. Accordingly, the electronic records being deposited with the HRDB 120 may be transmitted in an encrypted format. For example, health care record 720 may be encrypted using an encryption key stored on account instrument 150. Verification data 725 may be used to verify the EMR record corresponds to the records of claims processor $105_6$. In addition, in one embodiment, the authenticity of the deposit request may be verified using digital signatures 730 and 740. As illustrated, the request 610 includes a digital signature of both the patient 140 and the entity 105 making the deposit. However, in an alternative embodiment, the request may include only the digital signature (or other authorization data) from the patient 140.

FIG. 8 is a flow diagram illustrating actions performed as part of a deposit transaction, according to one embodiment of the invention. As illustrated, the method 800 represents a temporal sequence of events that occur during a deposit transaction. However, embodiments of the invention are not required to perform each of the steps according the particular sequence illustrated in FIG. 8. Steps illustrated by in block 810 refer to actions typically performed by a healthcare provider 105 and patient 140 to generate a deposit transaction. Steps 820 illustrated by block refer to actions typically performed by the HRDB 120 in response to such a request. At step 830, the entity generating the deposit request retrieves the account data 520 and routing data 530 from instrument 150. As described above, the routing data may specify a network-accessible address for the HRDB 120, and the account data may identify the patient's HRDB account. For example, routing data 530 may be a universal resource locator (URL) specifying a data communications protocol and DNS address for the HRDB 120. As described above, the patient key and routing info may be provided using a machine-readable access card. Alternatively, this information may be input to a computer system by the patient 140 or a representative of entity 105.

At step 840, the provider identification data 620 is retrieved and used to digitally sign the deposit request. At step 850, the provider submits the electronic medical record for deposit with the information supplied from steps 830 and 840. In one embodiment, the deposit request 610 includes the EMR record to be deposited (e.g., record 720), along with the authentication information (e.g., digital signatures 730 and 740).

Once the request 610 is generated, it is submitted over network 110 and received by HRDB 120. At steps 860 and 870, the HRDB 120 may be configured to verify the authenticity of the request by validating the digital signatures 730 and 740. If the validation fails, the HRDB 120 rejects the deposit request and the method 800 terminates. In an alternative embodiment, a deposit request may omit steps 840 and 860, allowing the patient 140 to authorize the deposit of an EMR record in his/her account without a digital signature from the entity 105 making the deposit.

If the signatures included with deposit request 610 are valid, then, optionally, the HRDB 120 may validate the request using a validation service provided by a healthcare payor 105₆ at step 890. Provided the validation checks are each successful, then at step 895, the EMR record associated with the deposit request 610 is deposited in the patient's HRDB account. At step 897, log data is generated for log/audit repository 155 to record details of the just completed deposit transaction.

Although not shown, the method 800 may additionally include actions such as error processing routines, or providing a deposit receipt back to the patient 140 and depositing entity 105, after a successful deposit transaction is competed.

FIG. 9 is a functional block diagram illustrating components of a distributed environment 900 used to initiate a withdrawal transaction with an account HRDB 120, according to one embodiment of the invention. Illustratively, the distributed environment 900 includes health care provider 105₂, interacting with patient 140 and account instrument 150. In one embodiment, when patient 140 receives health care related goods or services from provider 105₂, the patient provides the account instrument to provider 105₂ to authorize a withdrawal request 910. The withdrawal request 910 identifies the individual patient's account with the HRDB, along with routing data indicating the network accessible location of the HRDB. Additionally, provider identifier 620 may also be used to identify the physician or provider 105 making the withdrawal request. In one embodiment, the withdrawal request 910 may also include an indication of the EMR records being sought for the request such as a particular account, or may indicate that all available records, or an indication thereof, should be returned in response to the request.

Once generated, signed, and submitted, the HRDB 120 may be configured to process the withdrawal request 910 by verifying the identity of the requesting entity (using provider identifier 620 and account instrument 150) and retrieve the requested EMR records from health record repository 130. In addition, data related to the EMR records (e.g., an indication of the entity 105 that sent the withdrawal request 910) may also be returned in response to a withdrawal request.

Figure 10B:
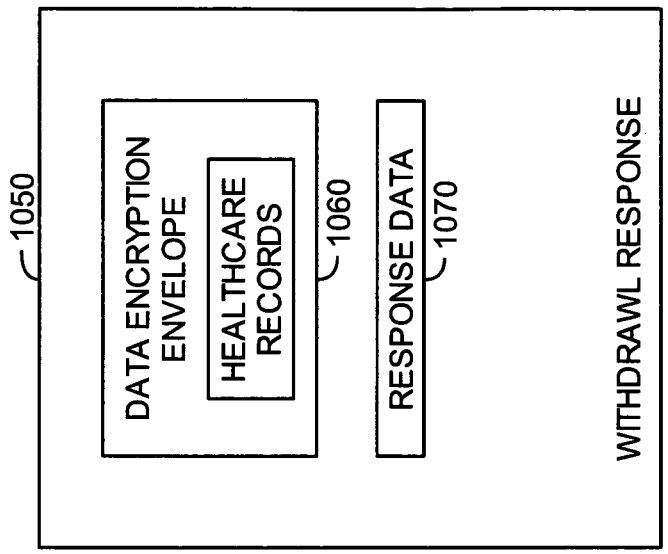
FIGS. 10A-10B illustrate a withdrawal request data structure and a response request data structure, according to one embodiment of the invention.
Figure 10A:
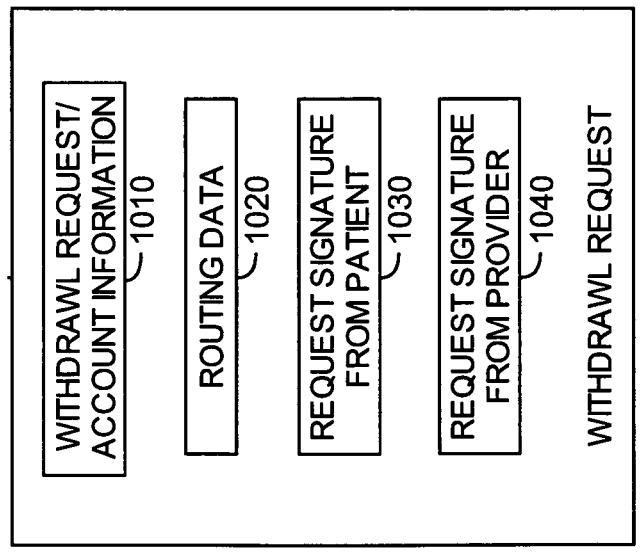
Figure 11:
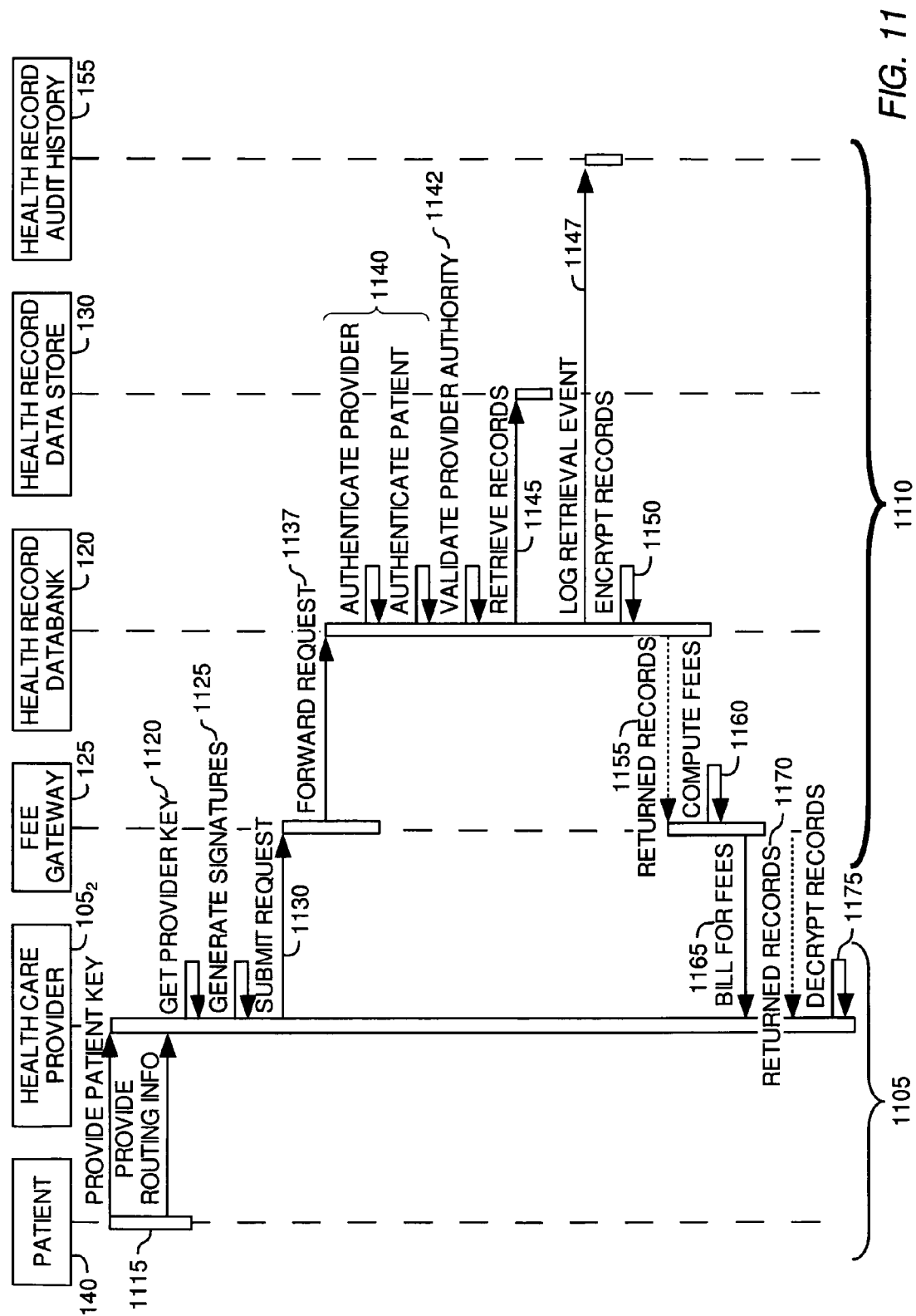
FIG. 11 illustrate a method for performing a withdrawal transaction with a health care records bank, according to one embodiment of the invention.

FIGS. 10A-10B illustrate a withdrawal request data structure 1000 (FIG. 10A) and a withdrawal response data structure 1050 (FIG. 10B), according to one embodiment of the invention. In one embodiment, withdrawal request data structure 1000 includes the actual withdrawal request 1010 indicating the patent's account that is the subject of the withdrawal request. Routing data 1020 specifies a network-accessible address for the HRDB 120. Signatures 1030 and 1040 provide the authenticating signatures from the patient 140 and care providing entity 105. Alternatively, the withdrawal request may omit signature 1040 and only include the authorizing signature 1030 from patient 140. Illustratively, withdrawal response data structure 1050 includes a response to a withdrawal request that returns the requested EMR records 1060 in an encrypted format. The encrypted record may be decrypted using a key included on account instrument 150. In one embodiment, the withdrawal response 1070 may indicate the EMR records that are being provided with the response 1050. This may include, for example, information related to the entity 105 that originally deposited the EMR records, fee data generated by fee/account gateway 125, or information related to additional services provided by HRDB 120.

FIG. 11 is a flow diagram illustrating actions performed as part of a withdrawal transaction. As illustrated, the flow diagram 1100 represents a temporal sequence of events that occur during a withdrawal transaction. However, embodiments of the invention are not required to perform each of the steps according the particular sequence illustrated in FIG. 11. Steps illustrated by block 1105 refer to actions typically performed by a healthcare provider 105 and patient 140, to submit a withdrawal transaction to HRDB. Steps illustrated by block 1110 refer to actions typically performed by the HRDB 120, in response.

At step 1115, the patient provides an account instrument 150 to the healthcare provider 105. For example, the account instrument 150 may be a magnetic strip that encodes account information 1010 and routing data 1020 identifying the HRDB 120 and the patient's account. At step 1120, the healthcare provider 105 retrieves a provider key. At step 1125, a withdrawal request generated and digitally signed using the provider key and the patient key. Alternatively, a patient 150 may authorize a provider to withdraw his/her EMR records, without also requiring a provider key and provider signature. So long as the patient 140 authorizes the withdrawal request 1000, the HRDB 120 may not require the care providing entity 105 to also sign the request. In another embodiment, access to the EMR records may be provided using a HRDB account identifier and password combination supplied by a patient 140.

In any case, once the request is generated it may be transmitted to HRDB 120 at step 1130. Once received, at step 1135, the fee gateway 125 may process the request to account for fees incurred by the provider 105 (or patient 140) as part of the withdrawal transaction. At step 1137, after being processed by the fee gateway 125, the withdrawal request is forwarded to the HRDB 120.

At step 1140, HRDB 120 may validate the request by verifying the patient account signature 1030 included with the request. If the patient signature 1030 is invalid, the request is rejected. Additionally, if the request 1000 includes a provider signature 1040, the validity of this signature may be verified. If the provider signature 1040 is invalid, the request is rejected. In one embodiment, access to a patient's HRDB account may be restricted (e.g., to one of multiple accounts), depending on the entity 105 making the request. In such an embodiment, at step 1142, the authority of the entity 105 to retrieve and view the records sought by the request 1000 is determined.

At step 1145, once the patient's authorization is confirmed, the HRDB 120 may be configured to retrieve the relevant health care records from records repository 130. The records retrieved may include all of the records, or some specified subset thereof. For example, a physician may wish to view only the electronic records that he/she created or only records storing most recent test results. At step 1147, a log of the request may be recorded in audit/history logs contained in the repository 155. At step 1150, the electronic medical records included in the response may be encrypted using the patient's encryption key. For example, if the account instrument 150 includes a public/private key pair, then the public key associated with the patient 140 may be used to encrypt the records returned with the response. Thereafter, only the private key encoded on the account instrument 150 can recover the encrypted data from the response. At step 1155, a withdrawal-response data structure is transmitted back to the fee gateway 125 where fees may be computed at step 1160. Additionally, in one embodiment, fees may be billed to an account established between the HRDB provider and health care provider 105. If so, at step 1165, any fees associated with the transaction are billed to the appropriate account. At step 1170, the requested EMR records are returned to the health care provider, and decrypted at step 1175. Once the records are decrypted, the healthcare provider 105 may use the EMR records as intended.

In addition to the common transactions described in FIGS. 6-11 embodiments of the HRDB 120 described herein may provide additional transactions and services as described below.

Multiple HRDB Accounts for an Individual

Embodiments of the invention described above provide an HRDB 120 configured to store a comprehensive collection of electronic medical records associated with a plurality of patients 140. In addition, common transactions (e.g., withdrawal and deposit) that a patient 140 may authorize for an HRDB account have been described. While this provides a patient 140 with a great deal of control over the records stored by the HRDB 120, embodiments of the invention may be configured to provide additional features.

Oftentimes, a patient 140 may want to authorize different access constraints for certain electronic records stored in the HRDB repository 130, or restrict the ability of an entity 105 to view the electronic medical records stored in the HRDB repository 130. For example, although a patient 140 may desire to provide a primary care physician (e.g., practicing at clinic $105_2$) relatively unrestricted access to the records in his/her HRDB account, it would be useful to allow a pharmacist to access only a subset of the records (e.g., records dealing with prescribed medications and over-the counter medications used by a patient 140). Similarly, the patient 140 may desire to limit a grocery store or a nutritional supplement provider to accessing records associated with allergies or possible cross-reactions between items purchased at the supplement provider and other medications. Given the choice between providing these types of entities unfettered access to the collection of EMR records in the HRDB 120, and no access, many patients may chose to not authorize any access at all (but still may allow deposit transactions).

Figure 12:
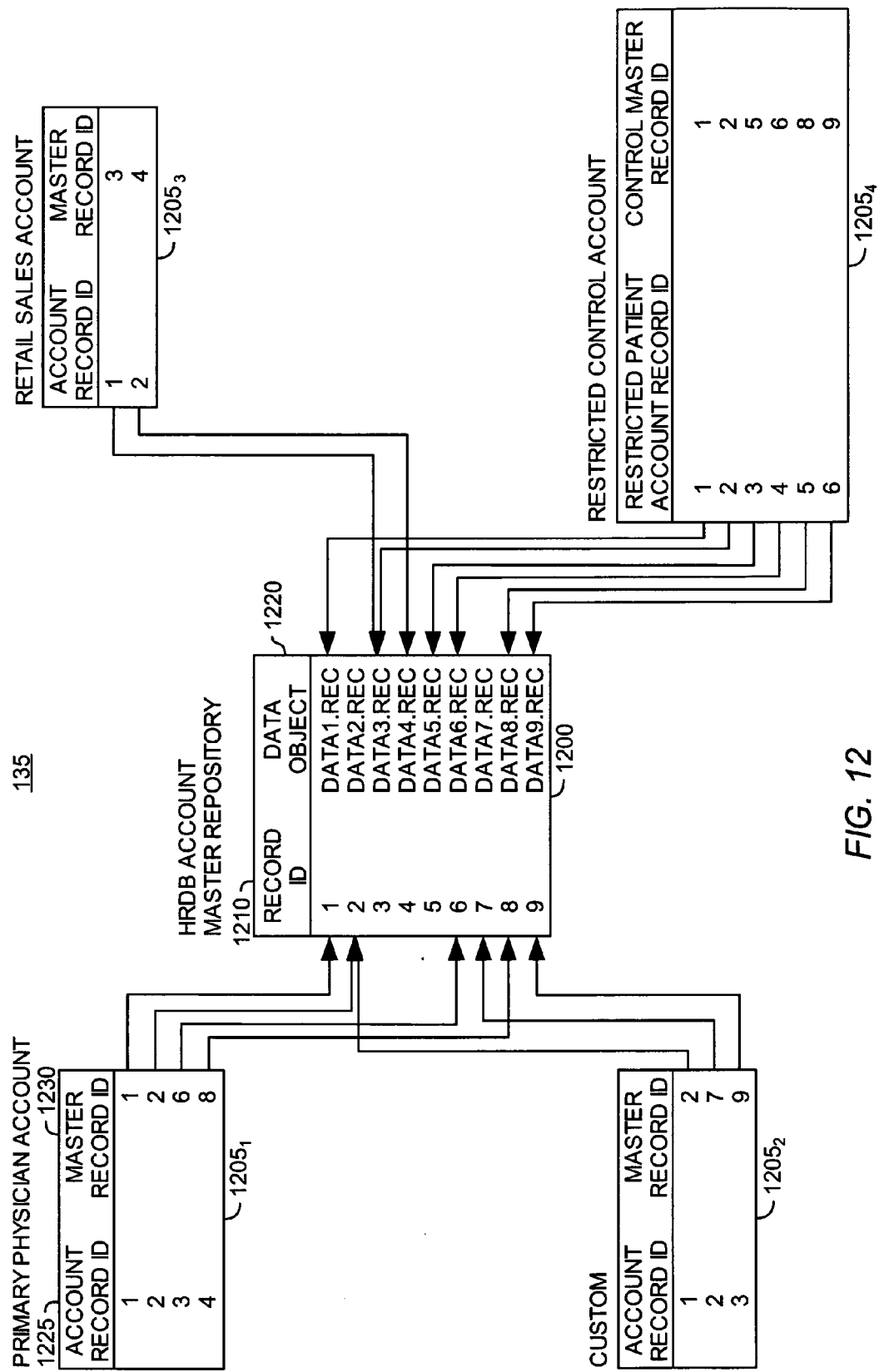
FIG. 12 illustrates the logical structure of multiple accounts within a healthcare records repository, according to one embodiment of the invention.
Figure 13:
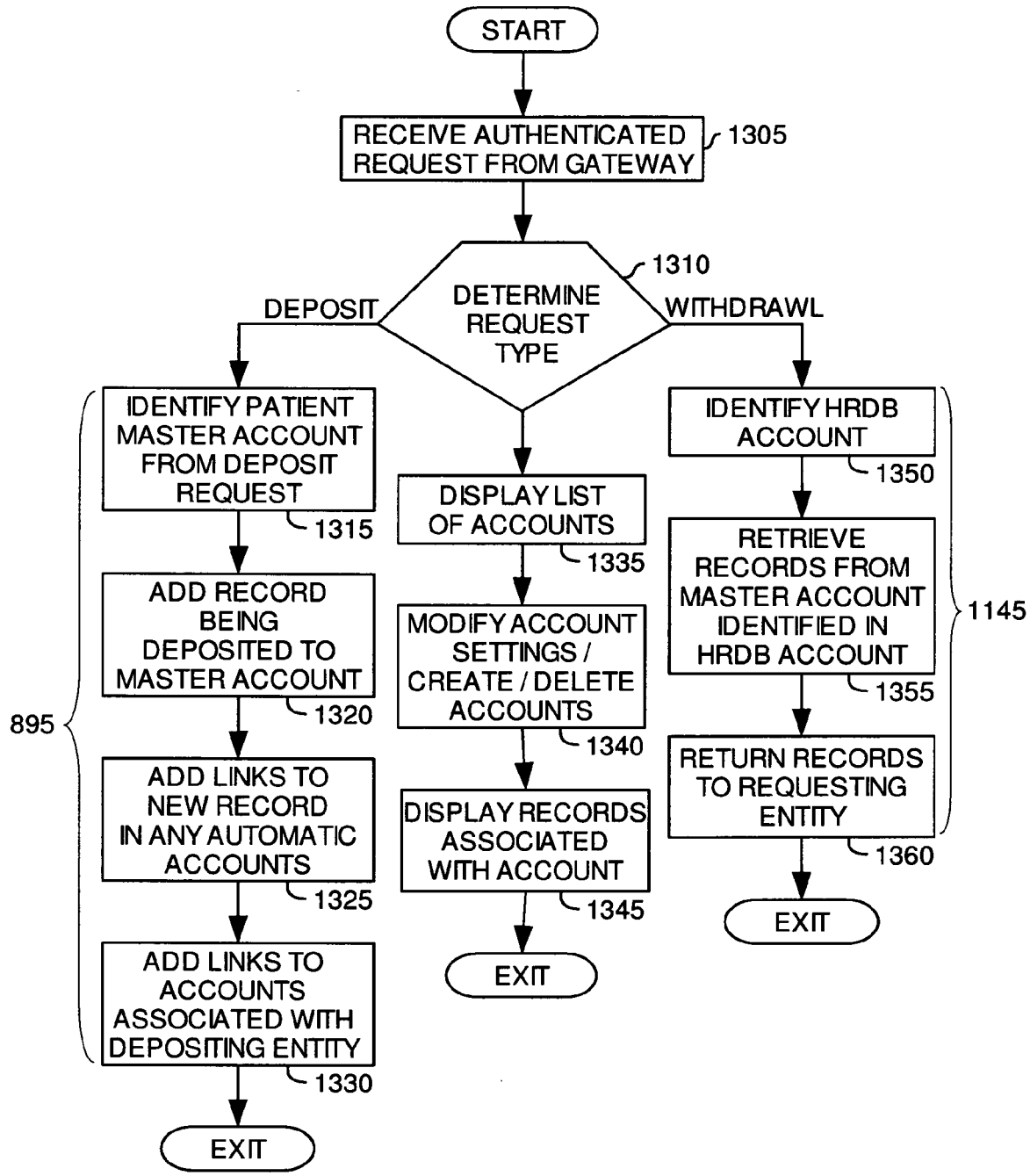
FIG. 13 illustrates a method 1300 for managing EMR records and sub-accounts 1205, according to one embodiment of the invention.

To address these scenarios, in one embodiment, the HRDB 120 may associate EMR records with one or more of multiple of sub-accounts. Each sub-account may include a subset of the available EMR records stored in the repository 135. FIG. 12 illustrates the logical structure used by the HRDB 120 to support multiple sub-accounts within a HRDB records repository 135, according to one embodiment of the invention. FIG. 13 illustrates three transactions authorized by the patient 140 to create, define, and control the multiple accounts illustrated in FIG. 12, according to one embodiment of the invention. Specifically, FIG. 13 illustrates the deposit and withdrawal of EMR records associated with a particular account, and the management by the user of EMR records and sub-accounts. In addition, a "restricted-control" account is described.

As described above, all of the EMR records associated with a patient's HRDB account are stored in a centralized repository 135, regardless of the source of the EMR records. For example, as illustrated in FIG. 1, a wide variety of entities 105 may deposit electronic medical records into data repository 130. Further, the patient 140 him/herself may contribute EMR records to the repository 135 stored in HRDB 120.

FIG. 12 illustrates a patient's account with the HRDB 120, utilizing a master repository 1200 and four sub-accounts $1205_{1-4}$. In one embodiment, each sub account identifies a plurality of records stored by the master repository 1200 for a particular patient. Illustratively, master repository 1200 includes a list of all of the records in a patient's HRDB account. In one embodiment, a patient's master repository 1200 may be implemented using a table in a database, configured according to a relational schema. As illustrated, each row of master repository 1200 represents an individual record in the Patients HRDB account, and each row in includes a record ID 1210 and the corresponding electronic medical record 1220 (shown in this example as files data1.rec through data9.rec, representing nine records in this HRDB account). Those skilled in the art will recognize, however, that this example is stylized to facilitate a description of the invention and that a schema used by a HRDB 120 to may differ form the one illustrated in FIG. 12.

In one embodiment, each sub-account 1205 identifies the records within the master repository 1200 associated with the particular sub-account 1205. For example, each sub-account $1205_{1-4}$ includes a table identifying one or more sub-account record ID values 1225 that lists the EMR records associated with particular the sub-account 1205. In this example, a database table is used to list the record IDs of the EMR records associated with the sub-account. Each row of the table identifies a corresponding record ID 1210 in the master repository 1200. By defining each sub-account 1205 as a collection of references to records in the master repository 1200, a patient 140 may define multiple sub-accounts that contain the same record(s), without requiring the HRDB 120 to store duplicate information.

In this example an HRDB sub-account $1205_1$ illustrates an account defined for a primary physician and includes four records identified by sub-account ID values 1, 2, 3, and 4. These four records resolve to records in the master repository 1200 with ID values 1, 2, 6 and 8. Each of these mappings is illustrated by the arrows leading from the sub-account $1205_1$ to records in the master repository 1200. Accounts $1205_{2-4}$ are similarly illustrated.

In one embodiment, the sub-accounts 1205 created for a patient's master repository 1200 may be provided by the HRDB 120 as part of a service offering. For example, the HRDB 120 may offer a number of predefined sub-accounts to capture records from common sources. For example, an individual's primary physician, a dentist, pharmacist, and other similar classifications may be provided. Also, accounts may be defined according to a given type of record being deposited (e.g., x-rays, lab-tests, prescriptions, vital statistics, dental-records, research participation, etc). The sub-accounts 1205 are not exclusive to one another, and a mix of provider-centric and data-centric sub-accounts 1205 may be provided. Doing so allows the patient's comprehensive collection of EMR records to be subdivided in numerous useful ways, and allows the patient 140 to tailor access to the records in his/her HRDB account.

In addition to sub-accounts 1205 provided by the HRDB 120, the patient 140 may be able to define custom sub-accounts 1205. For example, sub-account $1205_2$ illustrates a custom account, wherein the patient 140 has elected to include record ID's 2, 7 and 9 from the master repository 1200 in sub-account $1205_2$. In one embodiment, the patient 140 may specify the records included in a given sub-account 1205 using patient interface 410. For example, this could be provided using a graphical user interface that allows a patient 140 to drag records from the repository 1200 to any sub-account 1205. In addition, when authorizing an entity 105 to perform a deposit or withdrawal transaction, the patient 140 may specify what account should be used to process the request. In one embodiment, a patient 140 may also define rules to specify into which sub-accounts 1205 a new record deposited in his/her account should be automatically included.

Sub-account $1205_4$ illustrates an example of a "restricted-control" account. In one embodiment, the HRDB 120 may provide a sub-account $1205_4$ that restricts an individual from including or excluding certain electronic records deposited into the HRDB account. Such an account may be provided as special purpose accounts configured to contain a predefined set of electronic medical records, if they exist or have been provided to the HRDB. For example, access to a "restricted-control" sub-account may be defined for a primary care physician or for an insurance company underwriting a given insurance policy. In these cases, the patient 140 may choose to deny access to the HRDB account entirely, but if the entity 105 (e.g., an insurance company) is granted access, they will be provided access to the "restricted-control" account. Providing a "restricted-control" account may promote the growth of an HRDB 120 as an authoritative source for certain kinds of EMR records. For example, in some cases, a patient may attempt to conceal certain records (e.g., a diagnosis establishing a present medical condition). For this reason, the HRDB 120 may elect to guarantee that if certain types of EMR records are available in the repository 1200, they will be included in "restricted-control account" $1205_4$.

FIG. 13 illustrates a method 1300 for managing EMR records and sub-accounts 1205, according to one embodiment of the invention. The method begins at step 1305 after the health care records processing component 160 (from FIG. 1) receives an authenticated request from access/fee gateway 125. Step 1305 represents actions performed as part of steps 860-890 (for a deposit request) and steps 1140-1442 (for a withdrawal request).

At step 1310, the type of request being submitted to the HRDB is determined. As illustrated, the request may include a deposit request (in which case steps 1315-130 may be performed), a withdrawal request (in which case steps 1350-1360 may be performed), or a patient management request (in which case 1335-1345 may be performed).

For a deposit request, the method 1300 proceeds from step 1310 to step 1315, where the patient's master repository 1200 is identified. The electronic record 720 being deposited may then be assigned a record ID 1210 and added to the master repository 1200. As described above, the entity 105 submitting the deposit request, along with the date and time, may be recorded along with the EMR record 1220. At steps 1325 and 1330, links to this record may be created in one or more of the sub-accounts 1205. In one embodiment, the deposit request 1220 may indicate which sub-account(s) the record should be deposited into. For example, if a primary physician is submitting an EMR record 1220 for deposit, the record may automatically be deposited in a sub-account $1205_1$. Similarly, if accounts are defined for different record types (e.g., x-rays), then the record 1220 may be added to such a sub-account 1205 as well. As another example, a transaction record 320 recording the purchase of some nutritional supplement may automatically be entered in sub-account $1205_3$ storing prescription related medical records, as well as an account that allows access to information to determine any potential conflicting drug interaction. Thus, depending on how a patient has configured an HRDB account, links to the EMR record 1220 may be created in different sub-accounts 1205.

Returning to step 1310, if the request type is a withdrawal request, the method 1300 proceeds to step 1350. As described above, a patient 140 typically authorizes an entity 105 to access records stored in an HRDB account. At step 1350, the particular sub-account 1205 identified in the withdrawal request is determined. At step 1355, the records 1220 referenced by the sub-account are retrieved from the master account 1200. Once retrieved, these records are returned to the requesting entity in step 1360. As described above in reference to FIG. 11, the details of the withdrawal transaction may be logged in audit history logs contained in the repository 155.

In one embodiment, once authorized, an entity 105 may request any of the records in a sub-account 1205. However, once authorized to access a sub-account 1205, an entity may request fewer than all of the records identified therein. For example, a radiologist may request to view only a recent x-ray, rather than x-rays that have accumulated in a patient's HRDB account over a long period of time. Thus, a withdrawal request may include conditions requesting records according to when a record was created, the entity 105 that deposited the record, the content of the record, or other search conditions. Once identified, records in the sub-account 1205 satisfying any search conditions are returned to the entity that submitted the withdrawal request.

Returning to step 1310, if the request type is a patient-management request, the method 1300 proceeds to step 1335. In one embodiment, the HRDB 120 provides a patient 140 with the ability to create and delete sub-accounts 1205. At step 1335, a list of sub-accounts 1205 may be provided along with an indication of records available from the master repository 1200 that have been included in each sub-accounts 1205. At step, 1345, the patient modifies his/her account preferences by creating or deleting sub-accounts 1205, or adding and/or deleting links to records into the master repository form one or more sub-accounts 1205. For example, patient interface 410 may allow a user to drag records to/from an on-screen representation of a master repository 1200 to any defined sub-account 1205. Further, the patient 140 may also set up rules to define how new records are added to sub-accounts 120 as they are received in a deposit request 720. However, in one embodiment, the patient 140 may be prohibited from modifying records stored in a restricted-control account (e.g., sub-account $1205_4$, described above in reference to FIG. 12.).

Checkbook-Access

As described above, the account instrument 150 may include an access device (e.g., a plastic card with a magnetic-encoded strip) used to authorize transactions with the HRDB 120. In some embodiments, the account instrument 150 may provide each entity 105 with uniform access to the patient's HRDB account (or sub-account). In some cases, however, a patient may want to allow more limited access to an HRDB account. For example, the patient may not wish to rely on an entity 105 not overstepping the access that may be granted using a single, global account instrument 150.

To address these scenarios, in one embodiment, the HRDB 120 may provide a patient 140 with a plurality of portable, transferable access cards, checks, tickets, slips, etc. For simplicity, references herein are made to an "access check." It is to be understood, however, that an "access check" may be provided in the form of cards, checks, tickets, slips, or any other portable, transferable access granting device, including multiple token devices. For example, the access check may be provided as a plurality of smartcards, each configured to provide access to an HRDB account in a predefined manner. Alternatively, the access card may include a set of token devices that each includes an embedded RFID tag.

Each check may include an access key, which may be used to authorize an entity 105 to perform a specified transaction regarding an individual's HRDB account. The access granted by a given access check may specify, for example, what sub-accounts 1205 (or records) may be accessed, what transactions may be performed, and a time period during which access to a patient's HRDB accounts is authorized. In addition, some access checks may provide global access to a patient's HRDB account (until revoked). The access checks may be disposable, single use devices. Further, the access key may be different for each access check and may be used by the entity 105 to obtain a predefined level of access to an individual's patient's HRDB account, as described further below. Further, to authorize a given entity 105 to use an access check, the individual may be required to provide a personal identification number (PIN) or other form of an account access code to the HRDB before the entity 105 may access the individual's HRDB account.

In one embodiment, the HRDB 120 may provide a patient 140 with an account access checkbook. For example, the access checkbook may provide a physical book of preprinted paper slips or perforated tickets that may be torn from the book individually and provided to a care providing entity 105. Each slip may include a printed access key used to obtain access to the records in a patient's HRDB account. The access key may also be encoded on the check in a machine readable form using a bar code or magnetic strip, or magnetic ink may be used to print the access check. The access check may also include human-readable information indicating the patient's HRDB account and the access authorized by the access check.

Access checks allow a patient to provide an entity 105 with targeted and revocable access to the patient's HRDB account. For example, a patient 140 may desire to provide some level of access to any entity 105 for a limited number of days. This may be useful, for example, when a patient 140 seeks medical care while traveling, or when a patient seeks care from an entity 105 that does not have any relationship with the HRDB 120. As another example, one access check may be used to provide an emergency care provider with immediate access to a patient's medical history. Such an emergency access check may provide access to a sub-account 1205 that includes electronic medical records related to known allergies, current medications, or pre-existing medical conditions; each of which may be of critical importance to an emergency care provider making treatment decisions. Further, if a particular check, ticket, or slip etc., is lost, damaged or stolen, it may be revoked without disrupting access to an individual's HRDB account that has been authorized using others. In one embodiment, the access granted for a particular check/token device, may be predefined. For example, the predefined access may specify a number of days the entity 105 will be granted access, the types of records the entity 105 may access, or the account (or sub-account) that the entity 105 may access. In such a case, each check or token device may include an indication of what access a given check/token will grant to an entity 105 using the given check. Alternatively, an individual may configure an access check/token with the HRDB 120 in advance (e.g., using interface 410). In such a case, after configuring a particular access check or token device, the individual may inform the entity 105 regarding the level of access he/she has chosen to authorize for the particular access check or token device.

FIGS. 14A-14C illustrate an exemplary access check and two exemplary access tickets, according to one embodiment of the invention.

Referring first to FIG. 14A, which illustrates an exemplary access check $1400_1$ that includes routing data 1405, access key 1415, bar code 1410, and access information 1420. When an entity 105 is presented with an access check $1400_1$, the routing data 1405 informs the entity 105 of the network location of the HRDB. In one embodiment, routing data 1405 may provide a network-accessible location of the HRDB in the form of a URL that an entity 105 presented with access check $1400_1$ may enter into a web browser. In addition, access key 1415 provides a unique key for each check. As illustrated, the access key 1415 is shown as a hexadecimal character sequence. In one embodiment, each access key 1415 may be a cryptographically generated value, such that no two access checks 1400 share the same access key. Thus, the HRDB 120 may use the access key 1415 to verify that the entity 105 is in possession of a valid access check $1400_1$, and to restrict the actions of such an entity 105, in accordance with access constraints 1420.

In one embodiment, the access check $1400_1$ may be encoded in bar-code 1410, allowing an entity 105 to scan the access key 1415. Alternatively, the access key 1415 may be embedded in a token device, such as an RFID tag or smart-card. Alternatively, the access key 1415 may be entered using a web-based form on a web page accessed using routing data 1405. Illustratively, the access limits 1420 include access scope 1435 and access period 1425. In one embodiment access scope 1435 may identify what account, sub-account, or records that the check 1400 authorizes access to. Also, the access scope 1435 may specify what transactions are authorized by the access check. For example, an access check 1400 may specify a "deposit only" transaction. The check $1400_1$ illustrated in FIG. 14A grants access to the patient's primary care sub-account (e.g., account $1205_1$) for a period of thee days. Accordingly, once the entity 105 enters the access key 1415, the access granted by check $1400_1$ will be available to the entity 105 for a period of three days. In addition, the web-page accessed using routing data 1405 may request an entity 105 to provide additional input data to register or identify themselves with the HRDB 120 before performing transactions authorized by access check 1400. This allows transactions to be logged as originating from the entity 105 using the access key 1415.

FIG. 14B illustrates an exemplary deposit ticket $1400_2$. The deposit ticket includes routing data 1405 and magnetic strip 1435. In one embodiment, the magnetic strip may encode an access key 1415 used to authorize the transaction specified by constraints 1440 and 1445. Illustratively, the deposit ticket $1400_2$ may be used to authorize a single deposit transaction recording a retail purchase. Once used, the access key 1415 encoded by magnetic strip 1435 is no longer valid, and any further attempts to use the deposit ticket $1400_2$ will be rejected. The deposit ticket $1400_2$ may be useful, for example, to a patient 140 that would like a retail sales entity $105_4$ to deposit purchase records of supplements, vitamins, or medical supplies into an HRDB account. In addition to allowing an entity 105 (e.g., a primary care physician) to perform transactions regarding the HRDB account specified by an access check, the constraints specified may allow the entity 105 to engage in transactions with third parties. For example, an access check 1400 may allow a primary care physician to authorize a lab performing testing to deposit electronic records into an HRDB account.

FIG. 14C illustrates an example of an emergency access card $1400_3$. Like deposit ticket $1400_2$, the emergency access card $1400_3$ includes a magnetic strip 1435 used to encode an access key 1415. The actual access key 1415 is also listed as a hexadecimal sequence on the face of the emergency access card $1400_3$. Use instructions 1450 provide an emergency care provider with the appropriate instructions to use the access card $1400_3$ to obtain access to a patient's HRDB account. In the event an emergency care provider does not have the ability to scan the magnetic strip 1435, the routing information 1405 may be used to access a web-page where the access key 1415 may be manually entered. The access granted by the emergency access card $1400_3$ may allow a care provider to make more informed treatment decisions in an emergency, improving overall patient care.

In one embodiment, an HRDB 120 may allow an entity 105 to access an HRDB account using the emergency check $1400_3$ without also requiring the individual to provide an access code such as a PIN number. In such a case, the HRDB 120 may grant an access request using emergency access card $1400_3$ only when the request originates from certain, pre-authorized entities 105, such as a hospital emergency room or an urgent care clinic. For example, the HRDB 120 may use provider key information 240 to determine whether to grant a request generated using emergency access card $1400_3$.

Figure 15:
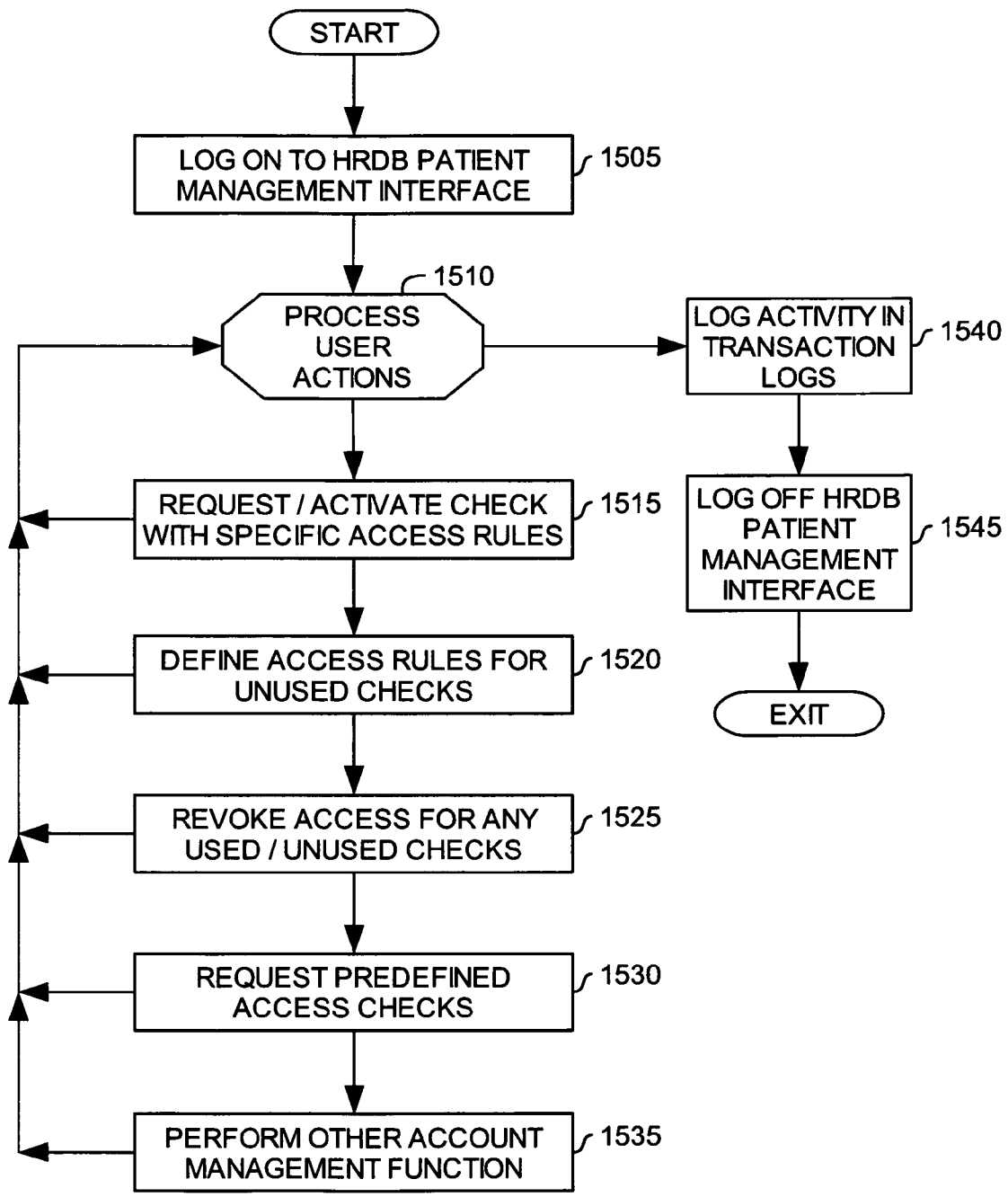
FIG. 15 illustrates a method for managing a plurality of access checks provided to a patent, according to one embodiment of the invention.

FIG. 15 illustrates a method for managing a plurality of access checks provided to a patent 140, according to one embodiment of the invention. The method 1500 begins at step 1505 where a user logs on to an HRDB patient-management interface, e.g., using the computer system 400 and patient interface 140 illustrated in FIG. 4.

While logged on, the patient 140 may select to perform any of the actions illustrated in boxes 1515-1530. For example, a user may request or activate a check with specific access rules (box 1515). In one embodiment, the patient 140 may be provided with a plurality of "blank" checks, each with a valid access key 1415. Each check 1400 may include a predefined access scope and validity period (1425 and 1430). The predefined access may include periods such as "1 day," "1 week" "1 transaction" or scope restrictions such as limiting access to a "dental account," "medications account" or other categories. Another possibility includes an "all access" or "permanent access," check 1400, which provides unrestricted access, until expressly revoked. A patient may wish to provide such an access check 1400 to a primary care physician. In one embodiment, although each check includes a valid access key 1415, until the patient 140 activates a given check 1400, it may not be used to access to the patient's HRDB account. Alternatively, some checks may be active (unless revoked) by default. For example, an emergency access ticket $1400_3$ may not require any a priori activation by the patient 140.

Alternatively, the patient 140 may define specific constraints for a particular check 1400 that does not specify predefined access limits. For example, a check $1400_1$ may include a valid access key 1415, but not include any specific time restrictions or access constraints. Using the patient interface 410, the user may customize access constraints to use for the given access key 1415. Additionally, on the actual printed check 1400, a patient 140 may write in the selected access constraints before providing such a check to a care providing entity 105.

Another account function provided by the HRDB 120 may allow a patient 140 to revoke any active or inactive access checks 1400 (box 1525). Because the access checks 1400 are meant to be disposable, revoking access to any particular check (e.g., because it is lost) is not disruptive to other active access keys 1415 being used by entities 105.

In one embodiment, access checks may be printed/manufactured by the HRDB 120 and mailed to a patient 140. Alternatively, the patient 140 may elect to download and print an access check 1400 directly (box 1530). The access check 1400 printed by a patient 140 may include a barcode allowing an entity 105 to scan the access key 1405 associated with the access check $1400_1$. Box 1535 represents other user selectable actions a patient 140 may perform, not illustrated by boxes 1515 through 1530 in FIG. 15.

In one embodiment, after completing a selected action, the activity is logged at step 1540. This data may be stored in the repository 155. For example, if a patient 140 has elected to activate an access check, the access key 1415 associated with the check 1400 is activated, and this status may be recorded in the repository 155. After completing any desired account maintenance, the patient 140 may conclude a patient management session and logoff from the patient interface 410.

Figure 16:
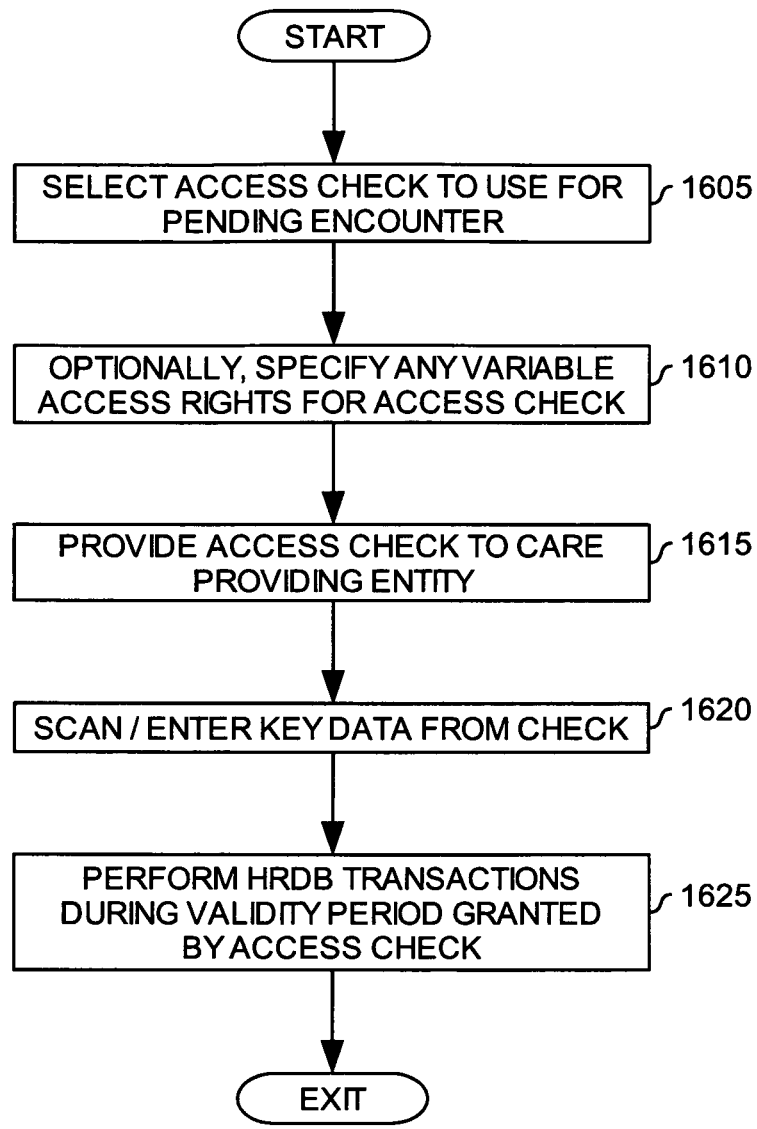
FIG. 16 illustrates a method 1600 a patient to use an access checkbook, according to one embodiment of the invention.

FIG. 16 illustrates a method 1600 a patient to use an access checkbook, according to one embodiment of the invention. The method 1600 begins at step 1605 where a patient 140 selects an access check 1400 to use for a pending encounter with an entity 105. At step 1610, the user may fill in any blank access constraints for the selected access check. For example, if the patient has specified that a particular check should be valid for 1 week; this may be handwritten onto the check 1435. Alternatively, a patient 105 may select to use access check 1400 with predefined access constraints preprinted on the check 1400. Additionally, if the access check is not activated by default, then the patient 140 may activate the check 1400 before providing it to entity 105.

At step 1615, the patient 140 provides the selected access check 1400 to the entity 105. For example, a check 1400 may be presented to an intake representative at a clinic $105_3$. At step 1620, the clinic representative may scan machine readable data encoded on the check, e.g., using a bar-code reader or magnetic card reader. Alternatively, if the entity 105 is unable to process the machine readable data, the clinic representative may manually enter the routing information 1405 and access key 1415. At step 1625, the entity 105 may engage in transactions (e.g., deposit and withdrawal transactions described above) with the HRDB 120, subject to any access constraints 1420 associated with the access key 1415. The specific transactions are logged in the audit/history repository 155. In one embodiment, once used, the access check 1400 may be discarded. Once the period 1425 provided by the access check 1400 lapses, the check may not be reused.

Figure 17:
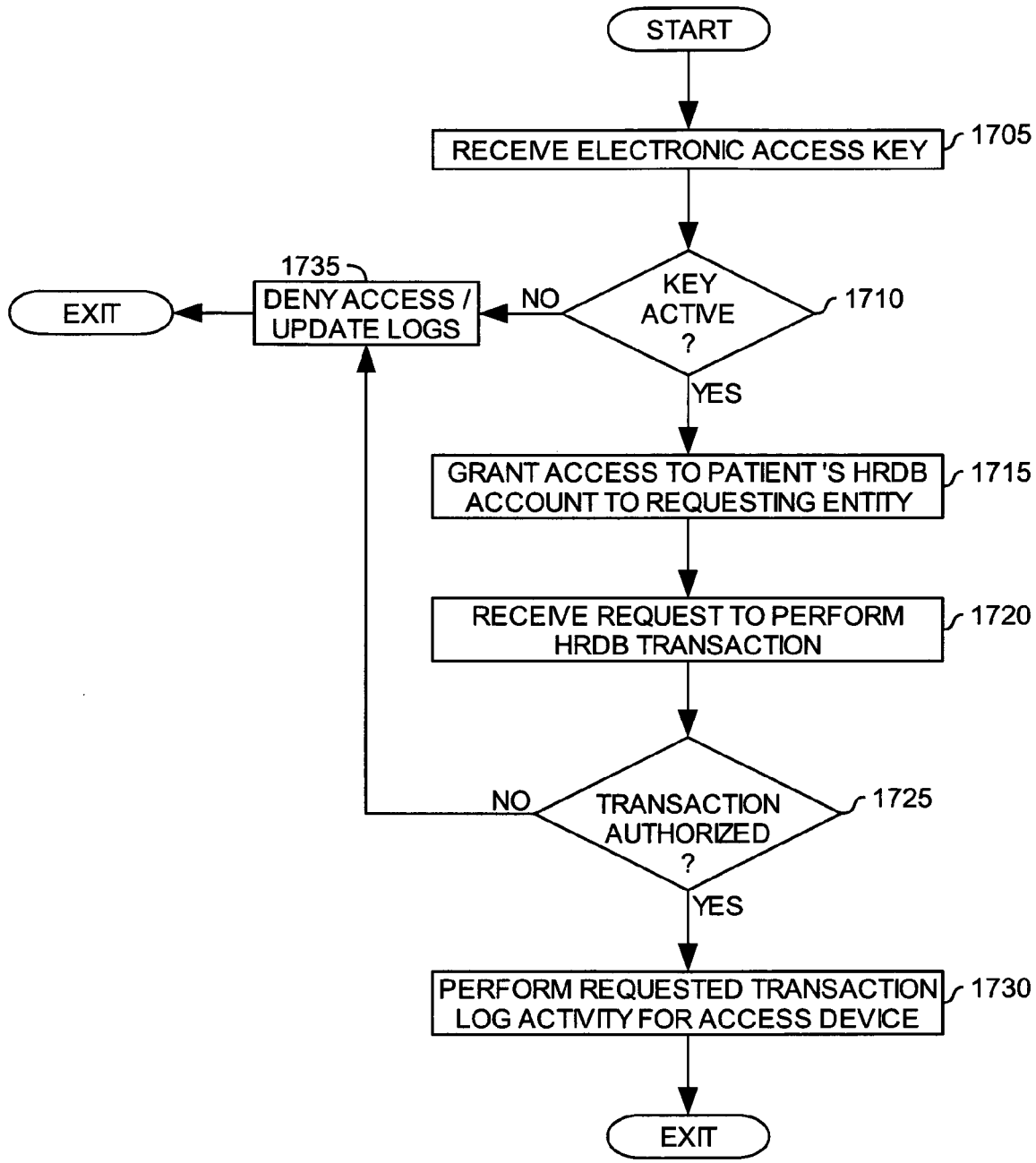
FIG. 17 illustrates a method for processing transactions authorized using an access check, according to one embodiment of the invention.

FIG. 17 illustrates a method for processing HRDB transactions authorized using an access check 1400, according to one embodiment of the invention. The method 1700 begins at step 1705 where the HRDB 120 receives a transaction request that includes an access key 1415 from a check 1400. At step 1710, the HRDB 120 determines whether the access key 1415 included in the request is active, if not the HRDB denies access and the method terminates (step 1735). For example, if the entity 105 provides an expired access key 1415, the request for access is rejected.

Otherwise, if an active access key 1415 is been provided, the HRDB 120 grants access to the associated patient's HRDB account (step 1715). In one embodiment, the entity 105 may register with the HRDB 120 before engaging in any transactions relative to patient's HRDB account. This allows any subsequent deposit or withdrawal transactions to be attributed to the correct entity 105 and recorded in the repository 155. Additionally, registration may allow the HRDB to provide additional services to a particular entity 105.

At step 1720, the HRDB 120 receives a request to perform a transaction (e.g., to withdraw a patient's HRDB records or to deposit new records into the patient's HRDB account). At step 1725, the HRDB 120 determines whether the access key 1415 provided by entity 105 authorizes the particular requested transaction, if not the HRDB denies access and the method terminates (step 1735). Otherwise, the HRDB performs the requested transaction (step 1730). So long as the access key 1415 is active, (e.g., during the specified validity period, or so long as not revoked by a user) the entity 105 may use the check 1400 to engage in transactions with the HRDB.

Monthly Account Statements

Figure 18:
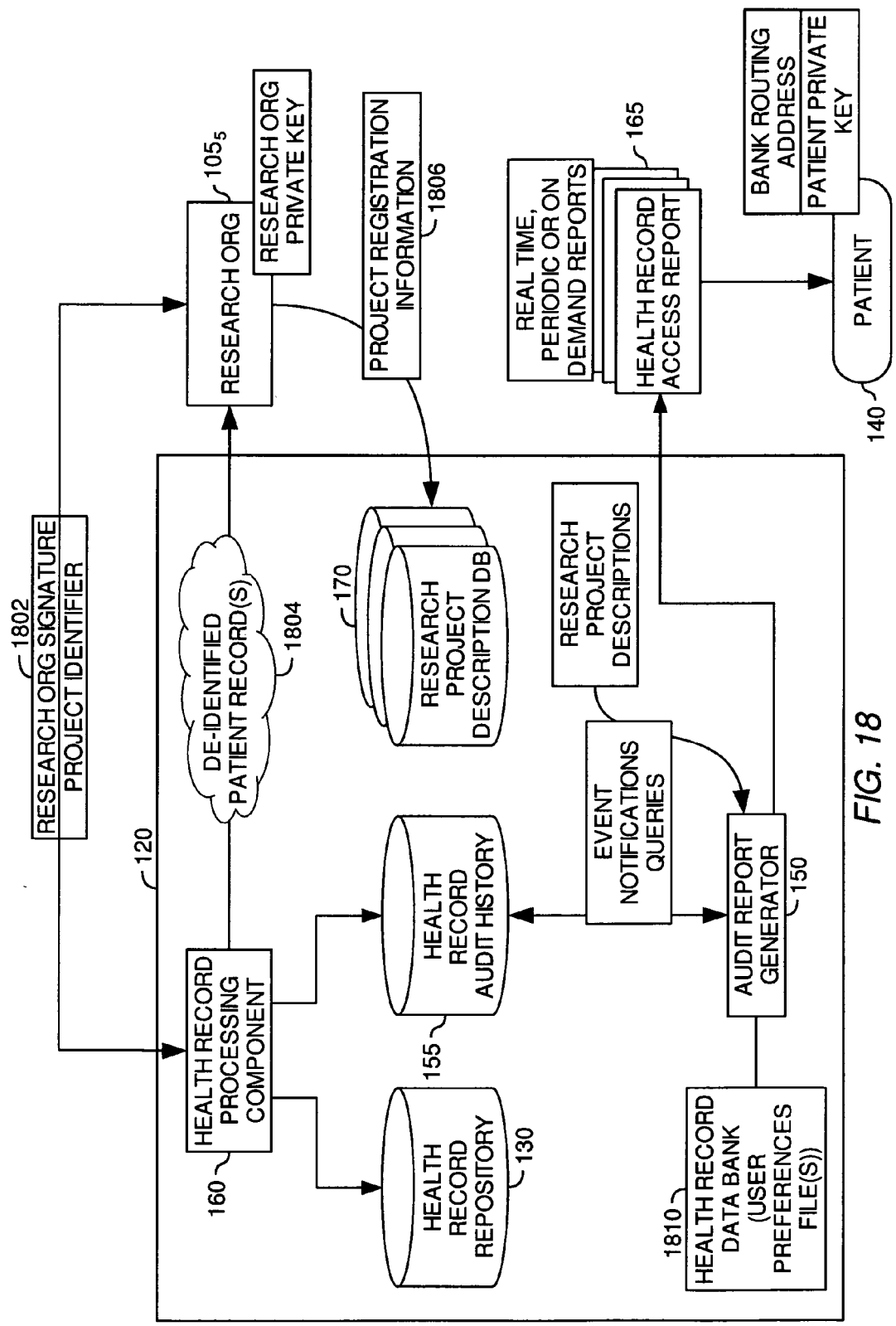
FIG. 18 illustrates one embodiment of a data processing environment in which reports reflecting data usage are generated and provided to individuals who data was used.

As described above, the HRDB provider may choose to provide a patient 140 with a statement detailing access and transactions related to an HRDB account. Referring now to FIG. 18, a block diagram is shown illustrating one embodiment of transaction environment 1800 in which various data can be captured or generated and then provided the appropriate to patients. In general, the diagram of FIG. 18 corresponds to FIG. 1, but has been simplified to highlight aspects relevant to providing patients account statements. Accordingly, like reference numbers correspond to like entities described above.

By way of illustration, FIG. 18 shows a research organization 105$_5$ making requests for data from the HRDB 120; although the requesting entity may be of any kind. In the case of a research organization 105$_5$ making requests with respect to a particular research project, the research organization 105$_5$ may be required to register the project. Accordingly, FIG. 18 shows a project registration event whereby the research organization 105$_5$ submits registration information 1806 to the HRDB 120 (the project registration, like other requests to the HRDB 120, may be handled by the health record processor component 160). The registration information 1806 is stored in the research project description database(s) 170. The registration information 1806 may include various details about the particular research project as well as a project identifier. The project identifier may serve as a key that can be used to join information from the health record audit history repository 130 and the research project description database 170 for purposes of generating health record access reports.

As was described above, the research organization 105$_5$ may initiate a request 1802 to the HRDB 120 for patient data. In some cases, the request may be specific to a particular research project. Accordingly, the research organization 105$_5$ may include the appropriate project identifier with the request 1802. Upon receiving the request 1802, the HRDB 120 may operate to retrieve and return the appropriate data. In one embodiment, it may be desirable or necessary to maintain the anonymity of the patients whose records are being returned to the research organization. For example, a patient may have specified a security policy that allows all or a select portion of their information to be released, so long as the patient's identify is not discernible from the information released. Accordingly, the HRDB 120 may take appropriate steps to "anonymize" any records 1804 before returning the same to the requesting entity (in this case the research organization 105$_5$).

In one embodiment, all or some of the information captured and/or generated by the HRDB 120 that corresponds to particular patients may be provided to the respective patients in the form of health care record access reports 165. It is contemplated that the patient may specify various attributes related to the reports 165 in a user preferences file 1810. Each user preferences file 1810 may be populated by the respective patient using a Web browser, for example.

Illustrative preferences that may be specified include the conditions under which the reports 165 are provided to the respective patients. For example, in one embodiment a report 165 is provided to a patient 140 at a predefined frequency (e.g., weekly, monthly, yearly). In another embodiment, reports 165 are provided to a patient 140 on demand. In other words, the patient 140 may explicitly initiate a request for a report 165. In another embodiment, a report 165 may be provided to a patient 140 in response to the occurrence of a predefined event. For example, the patient 140 may have elected to receive a report 165 any time a request is made for the patient's data. Alternatively, the patient 140 may have requested to receive the report 165 only when specified data (e.g., particularly sensitive data) in the patient's records is requested. Alternatively, the patient 140 may have requested to receive the report only when a particular research organization requests the patient's data.

In addition to specifying the conditions under which a patient receives a report, patients may also specify the manner in which reports are received. For example, the patient may specify that his/her reports are sent via e-mail, regular mail, text messaging, etc. Further, patients may also specify which data is to be included in the report 165. One embodiment of a report 165 is shown in FIG. 19.

The report 165 in FIG. 19 is arranged as a table having a plurality of columns 1902$_N$ and rows 1904$_N$. The columns include a date column 1902$_1$ (for storing date values corresponding to the date of activity), a records column 1902$_2$ (for storing a description of the affected patient records), a requestor column 1902$_3$ (for storing a name of the entity or individual accessing the record), a reason column 1902$_4$ (for storing a description of the purpose for accessing the record), a "delegated from" column 1902$_5$ (for storing an indication of a party to whom the requestor provided the record), a "requestor type" column 1902$_6$ (for storing a description of the entity or individual accessing the record) and a "more info" column 1902$_7$ (for storing various other information that may be relevant to the record accessed). Of course, these columns are merely exemplary and other reports may contain additional or fewer columns.

In one embodiment, each row 1904$_N$ of the report 165 corresponds to particular access of the respective patient's data. For example, a first row 1904$_1$ corresponds to a record retrieval (withdrawal) by a personal physician (Dr. Frank Smith) as part of a scheduled appointment. A second row 1904$_2$ corresponds to research use of patient information. In this case, the "more info" column 1902$_8$ includes a link to findings based on this research. Thus, by clicking on the "Findings" link the patient may be navigated to a screen (e.g., web site) where results of the research or posted. In some cases, the patient may be given a user ID and password to access findings specific to the patient's data (assuming such data exists). A third row 1904$_3$ corresponds to a record access in which one research organization (ACME Pharmaceuticals) made the retrieved patient information available to another organization (Medical Research Associates) performing clinical trials. Thus, is contemplated that a requestor of patient data may be required to agree to notify the HRDB 120 in the event that any patient data provided to requestor is subsequently provided by the requestor to a third-party. More generally, the requester may be required to agree to provide the HRDB 120 with any variety of predefined notifications, including notifications of regarding how the data is being used, by whom the data is being used, any finding based on the data, etc. These agreements may be a contractual condition to the requester receiving the request of patient data. Row 1904$_3$ also contains a link ("clinical trial") in the "more info"

column $1902_7$ which the patient can click on to navigate to a site where the patient can sign up to participate in trials for the drug being studied (i.e., "Drug X"). The last row $1904_4$ in the exemplary report 165 is an example of a new record deposit, as reflected by the word "deposit" in the Records column $1902_2$. As an alternative, it is contemplated that the report 165 may include an additional column for containing a value representative of the access type (e.g., withdrawal, deposit, update, delete, etc.).

The foregoing are merely exemplary embodiments. Persons skilled in the art will recognize other embodiments within the scope of the invention. For example, in one embodiment, a patient may receive separate reports for each of a plurality of accounts (multiple accounts were described above). In one embodiment, the patients are required to pay for a service, which provides them the reports 165. All such embodiments, and others, are broadly contemplated.

Fee Based-Services/Data Research

As described above, the fee gateway of 125 may be configured to manage fees associated with the HRDB. In one embodiment, the HRDB 120 includes a fees database 135 containing one or more fee schedules 134. It is contemplated that a fee schedule may be provided for each patient 140, each patient account, each entity 105, each type of data or for any other definable basis for fee calculation. For convenience, reference may be made to a singular fee schedule 134.

Figure 20:
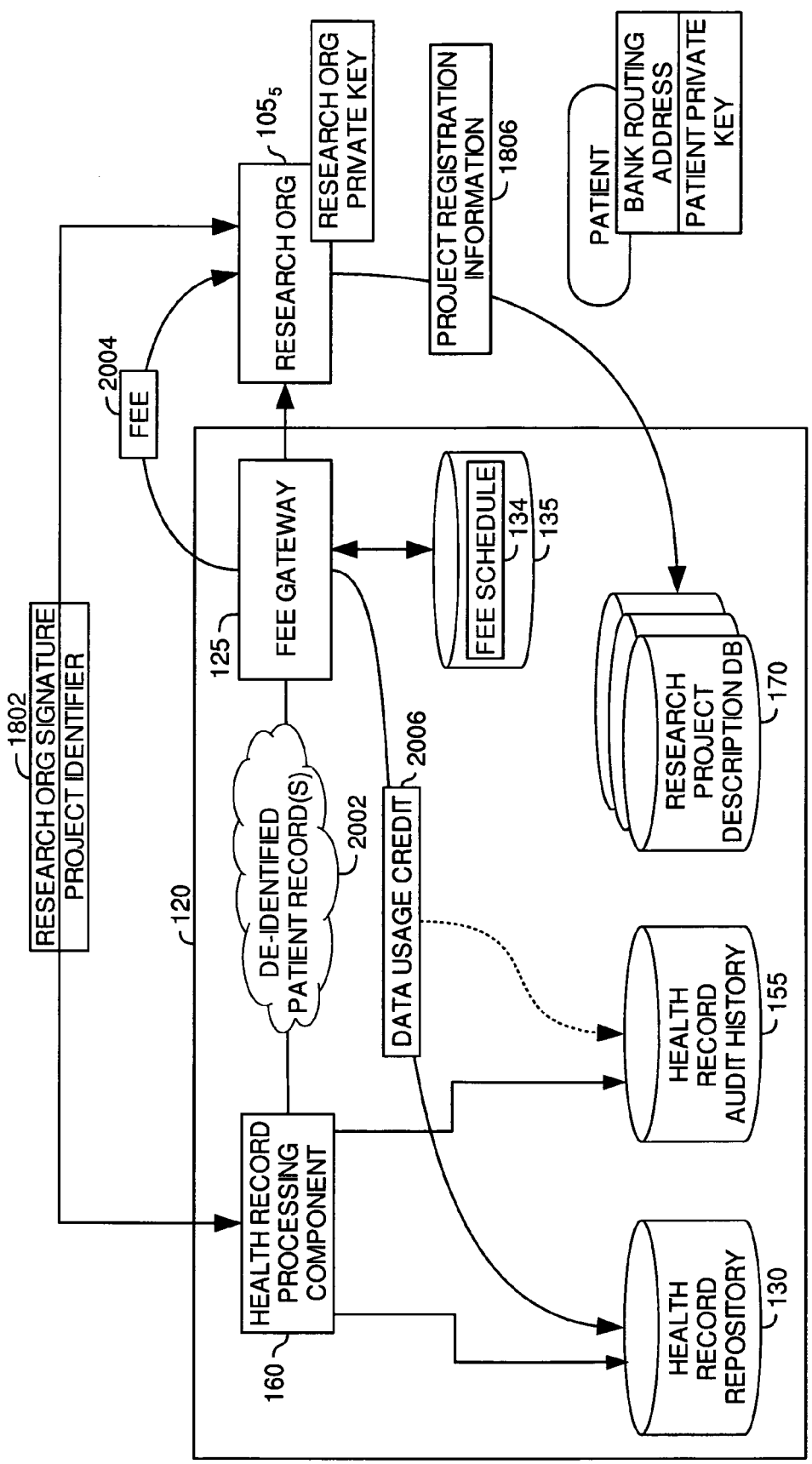
FIG. 20 illustrates one embodiment of a health record account history report.

Referring to FIG. 20 one embodiment of a data processing environment 2000 is shown in which fees are calculated for data accesses made by a research organization $105_5$. However, the entity to be charged a fee may be any entity requesting patient records, including any of the entities described above with respect to FIG. 1. Thus, in alternative scenario, the requesting entity is a health care provider requesting data for a patient it is treating. Many of the elements shown in FIG. 20 correspond to those described above with reference to FIG. 1 and FIG. 18. Accordingly, like-numbered elements correspond and are not described again in detail.

Illustratively, the research organization $105_5$ submits a request 1802 on the basis of a registered project. The processing component 160 receives the request and retrieves the appropriate patient record(s) 2002. The patient records 2002 are provided to the fee gateway 125 which then determines (e.g., calculates) a fee to be charged to the research organization $105_5$. In one embodiment, the fee gateway 125 determines the fee by accessing appropriate fee schedule 134. The determined fee 2004 and the patient records 2002 are then returned to the requesting entity (in this case the research organization $105_5$). In one embodiment, the determined fee 2004 is first provided to the research organization before the requested patient records 2002 are returned. The research organization may then accept or reject the fee 2004. If the research organization accepts the fee the HRDB 120 then provides the requested patient records 2002 to the research organization. On the other hand, the research organization may reject the fee and forgo receipt of the requested patient records 2002.

Payment of the fee 2004 by a requesting entity may be handled in any of a variety of ways. For example, the requesting entity may maintain an account with the HRDB 120. For each fee incurred by the requesting entity the gateway 125 may record the fee in the requesting entity's account. A statement may then be provided to the requesting entity on a periodic basis (e.g., monthly), whereupon the requesting entity may remit payment. Alternatively, the requesting entity may be required to pay at the time of the request 1802. In this case, payment may be made by collecting the requesting entity's credit card information via a secure network connection, for example. In another embodiment, the requesting entity may be on a flat fee subscription plan with the HRDB 120. The flat fee subscription plan may give the requesting entity access to all or some subset of the available data maintained by the HRDB 120.

In one embodiment, the requesting entity 105 may negotiate a license for the some subset of patient data for a period of time. This may be particularly viable where the HRDB 120 is continually updating the relevant data of interest to the requesting entity. For example, in exchange for an exclusive license to the subset of data (including updates), the requesting entity may agree to pay a periodic royalty until the expiration of the predefined period of time, at which point the license terminates and access to the data (or at least any future updates) by the requesting entity 105 is cut off. Alternatively, rather than establishing a predefined period of time, the requesting entity may "check out" various patient data (including updates) for an unlimited period of time so long as the requesting entity continues to make periodic payments. It is contemplated that data may be checked out by only a single requesting entity at a given time, or that multiple requesting entities may check out the same data at the same time.

Regardless of whether the fee is paid in lump sum or over time, any number of models for determining the value of the total fee 2004 are contemplated. Thus, in one embodiment, the fee may be determined on the basis of the type of data being requested. Such a model may be premised on the presumption that different data have different values to a requesting entity. For example, data pertaining to a very rare disease is likely to be in short supply. Accordingly, given the smaller pool of available data pertaining to such a disease, a requesting entity may be willing to pay more for such data.

In another embodiment, the fee is dependent on the volume of data. For example, each record may be assigned a particular cost and the total fee 2004 is the sum of the costs. The per record cost may be the same for each record, or may be different for each record.

In another embodiment, the fee is dependent on the cost to the HRDB 120 associated with the storage and maintenance of the records. This cost may be driven, at least in part, by the type of data. For example, an image file from a microarray device would likely cost more to retrieve then a simple text file. Also, the image file would likely cost more to store given that more storage space would be needed.

In another embodiment, the fee is dependent on specialized and selectable services provided by the HRDB 120 on request. For example, the requesting entity may require data normalization so that the patient records returned use terminology and codes consistent with those used by the requesting entity.

In another embodiment, the fee is dependent on a length of session (i.e., network connection with the HRDB 120) during which the requesting entity queries the available patient data. In other words, the requesting entity's access may be metered on the basis of time and once the requesting entity signals that a session is over, a session fee can be calculated on the basis of the total length of the session. For example, a requesting entity may be charged a set price per minute, hour or other quantum of time.

In another embodiment, the fee may be negotiated for a particular request or subset of data. For example, upon receiving a request for patient data from a requesting entity, the health record databank 120 may contact the patient(s) whose data is being requested and invite the patient(s) to participate in a negotiation with the requesting entity. In one embodiment, such a negotiation may be conducted online over a secure connection. The patient(s) and the requesting entity may alternately submit offers and counter offers until a fee can be agreed upon or until one of the parties terminates the negotiation.

In another embodiment, the fee may be determined in an auction environment in which multiple requesting entities bid on the same data. The highest bidder may be given exclusive access to the data. The auction may be conducted by the HRDB 120, or by a third-party.

In addition to, or alternatively to, the HRDB 120 receiving compensation from the requesting entities, it is also contemplated that the patients receive a credit for the use of their data. Accordingly, FIG. 20 illustrates with the gateway 125 calculating and storing a data usage credit 2006 to the health record repository 130 and/or the health record audit history repository 155. In one embodiment, the patients are notified of any fees their data has generated in a report generated by the report generator 150 (FIG. 1), such as the reports 165 described above with respect to FIGS. 18-19. Thus, in addition to contain information about usage of their data, the reports 165 may indicate the fees generated by such usage. Alternatively, the patients may be notified in a separate report.

The data usage credit 2006 for a given patient may be determined according to a variety of ways, including on the basis of criteria stored in a fee schedule 134. In one embodiment, each patient contributing to the patient records 2002 may simply receive an equal share of the total fee 2004 charged to the requesting entity 105 (less, perhaps, some portion paid to the HRDB 120). In another embodiment, the credit 2006 is determined as a function of the total amount of data returned to the requesting entity 105. For example, if a given patient's data included with the patient records 2002 returned to the requesting entity 105 makes up 3% of the returned patient records 2002, then the given patient may receive 3% of the fee 2004 charged to and paid by the research organization.

In another embodiment, the usage credit 2006 may be a function of the particular type of data being provided to the requesting entity 105. As was noted above, some data may be more valuable to the requesting entity 105. Accordingly, the patients who data is considered more valuable may be paid a premium over patients with less valuable data.

In several of the foregoing embodiment, the patient whose data is being requested is not charged a fee associated with the storage of their data of the transaction in which their data is accessed. In fact, in some embodiments the patients are compensated for use of their data. However, in other embodiments, the patient is charged for either the storage or retrieval (or both) of their data. Further, although embodiments have been described separately, any combination of fee-generation models is contemplated.

CONCLUSION

Embodiments of the invention provide for patient controlled storage, management, and retrieval of electronic medical records. According to embodiments of the invention, data providers (including government and private organizations) can implement large-scale, electronic medical records systems that can provide an authorized entity with a comprehensive set of electronic medical records for a given patient. The anticipated savings of such an infrastructure are dramatic, driven in part by reduction in redundant or unnecessary tests and procedures and by an increased efficiency from the elimination of record duplication and transport. In addition to reducing costs, providing on-demand access to a comprehensive set of electronic medical records may improve the quality of care experienced by patients, as physicians will have access to more information when making treatment decisions.

While the foregoing is directed to embodiments of the present invention, other and further embodiments of the invention may be devised without departing from the basic scope thereof, and the scope thereof is determined by the claims that follow.

What is claimed is:

1. A computer-implemented method of controlling access to a plurality of electronic medical records related to a plurality of individuals, comprising:
    configuring a network-accessible storage repository to store the plurality of electronic medical records, wherein the electronic records for a given individual are associated with an electronic health records account (EHR account);
    providing the individual with at least one portable, EHR account access device, wherein the access device includes a predefined authorization key that authorizes a plurality of requesting entities with access to the EHR account when presented with the access device;
    receiving, over a data-communications network, a request from one of the requesting entities, wherein the request includes at least one transaction to be processed, the predefined authorization key from the access device given to the requesting entity by the individual, and a predefined requestor identification identifying the requesting entity, wherein the access device authorizes the entity presented with the access device to (i) perform a deposit transaction, wherein the deposit transaction submits additional electronic records associated with the individual stored in the network-accessible storage repository or (ii) to retrieve electronic records associated with the individual from the network-accessible repository;
    authorizing the request based on both the predefined authorization key and the predefined requestor identification key;
    performing the at least one transaction included in the request by use of one or more computer processors for the EHR account;
    for each record accessed by one of the requesting entities, generating a report, wherein the generated report includes a listing of requests to access records associated with the individual and the respective requestor identification for each request; and
    providing the reports to the individual.

2. The method of claim 1, wherein the access device provides a cryptographic key used to identify the access device and to identify the predefined authorization established for the access device.

3. The method of claim 1, wherein the predefined authorization specifies a period of time to grant access to the EHR account to the entity presented with the access device.

4. The method of claim 1, wherein the at least one access device comprises a plurality of preprinted paper slips that may be individually presented to different entities, and wherein each slip includes a different cryptographic key used to distinguish the preprinted paper slips from one another, and wherein each of the preprinted paper slips identifies the predefined authorization specified for a given slip.

5. The method of claim 1, wherein the access device includes a machine-readable access key selected from at least one of a bar-code, magnetic ink, magnetic strip, or character sequence.

6. The method of claim 1, wherein the access device provided to an individual specifies the predefined authorization for the access device.

7. The method of claim 1, wherein the individual selects the predefined authorization for a given access device, prior to presenting the given access device to the entity.

8. The method of claim 1, wherein the access device is revocable, and wherein a revoked access device will fail to provide the entity presented with the revoked access device access to the EHR account.

9. The method of claim 1, wherein at least one account device comprises a token device with an embedded electronic device that is used to encode the account identifier and access key.

10. The method of claim 1, wherein at least one account device may be used by certain predetermined entities to obtain access to the EHR account.

11. A non-transitory computer-readable medium containing a program, which when executed by a processor performs operations for managing access to a plurality of electronic medical records related to a plurality of individuals, the operations comprising:
configuring a network-accessible storage repository to store the plurality of electronic medical records, wherein the electronic records for a given individual are associated with an electronic health records account (EHR account);
providing the individual with at least one portable, transferable EHR account access device, wherein the access device includes a predefined authorization key that a plurality of requesting entities with access to the EHR account when presented with the access device;
receiving, over a data-communications network, a request from one of the requesting entities, wherein the request includes at least one transaction to be processed, the predefined authorization key from the access device given to the requesting entity by the individual, and a predefined requestor identification identifying the requesting entity, wherein the access device authorizes the entity presented with the access device to (i) perform a deposit transaction, wherein the deposit transaction submits additional electronic records associated with the individual stored in the network-accessible storage repository or (ii) to retrieve electronic records associated with the individual from the network-accessible repository;
authorizing, by operation of the processor, the request based on both the predefined authorization key and the predefined requestor identification key;
performing, by operation of the processor, the at least one transaction for the EHR account;
for each record accessed by one of the requesting entities, generating a report, wherein the generated report includes a listing of requests to access records associated with the individual and the respective requestor identification for each request; and
providing the reports to the individual.

12. The non-transitory computer-readable medium of claim 11, wherein the access device provides a cryptographic key used to identify which particular access device is presented to the entity and to identify the predefined authorization established for the access device.

13. The non-transitory computer-readable medium of claim 11, wherein the predefined authorization specifies a period of time to grant access to the EHR account to the entity presented with the access device.

14. The non-transitory computer-readable medium of claim 11, wherein the at least one access device comprises a plurality of preprinted paper slips that may be individually presented to different entities, and wherein each slip includes a different cryptographic key used to distinguish the preprinted paper slips from one another, and wherein each of the preprinted paper slips identifies the predefined authorization specified for a given slip.

15. The non-transitory computer-readable medium of claim 11, wherein the access device authorizes the entity presented with the access device to perform a deposit transaction, wherein the deposit transaction submits additional electronic records associated with the individual stored in the network-accessible storage repository.

16. The non-transitory computer-readable medium of claim 11, wherein the access device authorizes the entity presented with the access device to retrieve electronic records associated with the individual from the network-accessible repository.

17. The non-transitory computer-readable medium of claim 11, wherein the access device includes a machine-readable access key selected from at least one of a bar-code, magnetic ink, magnetic strip, or character sequence.

18. The non-transitory computer-readable medium of claim 11, wherein the access device provided to an individual specifies the predefined authorization for the access device.

19. The non-transitory computer-readable medium of claim 11, wherein the individual selects the predefined authorization for a given access device, prior to presenting the given access device to the entity.

20. The non-transitory computer-readable medium of claim 11, wherein the access device is revocable, and wherein a revoked access device will fail to provide the entity presented with the revoked access device access to the EHR account.

21. The non-transitory computer-readable medium of claim 11, wherein at least one account device comprises a token device with an embedded electronic device that is used to encode the account identifier and access key in a machine readable form.

22. The non-transitory computer-readable medium of claim 11, wherein at least one account device may be used by certain predetermined entities to obtain access to the EHR account.

* * * * *